US012680106B2

(12) United States Patent
Dodds et al.

(10) Patent No.: US 12,680,106 B2
(45) Date of Patent: Jul. 14, 2026

(54) STEM RUST RESISTANCE GENE

(71) Applicant: COMMONWEALTH SCIENTIFIC AND INDUSTRIAL RESEARCH ORGANISATION, Acton (AU)

(72) Inventors: Peter Norman Dodds, Canberra (AU); Timothy Charles Hewitt, Canberra (AU); Rohit Mago, Canberra (AU); Narayana Mithur Upadhyaya, Canberra (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 0 days.

(21) Appl. No.: 18/025,219

(22) PCT Filed: Sep. 8, 2021

(86) PCT No.: PCT/IB2021/000608
§ 371 (c)(1),
(2) Date: Mar. 8, 2023

(87) PCT Pub. No.: WO2022/053866
PCT Pub. Date: Mar. 17, 2022

(65) Prior Publication Data
US 2023/0272412 A1 Aug. 31, 2023

Related U.S. Application Data

(60) Provisional application No. 63/127,220, filed on Dec. 18, 2020, provisional application No. 63/076,153, filed on Sep. 9, 2020.

(51) Int. Cl.
| | |
|---|---|
| *A01H 5/10* | (2018.01) |
| *A01H 1/00* | (2006.01) |
| *A01H 6/46* | (2018.01) |
| *C12N 15/82* | (2006.01) |
| *C12Q 1/6895* | (2018.01) |

(52) U.S. Cl.
CPC ....... *C12N 15/8282* (2013.01); *A01H 1/1255* (2021.01); *A01H 5/10* (2013.01); *A01H 6/4672* (2018.05); *A01H 6/4678* (2018.05); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 11,576,326 | B2 | 2/2023 | Csiro |
| 2022/0112512 | A1 | 4/2022 | Lagudah et al. |

FOREIGN PATENT DOCUMENTS

| | | | |
|---|---|---|---|
| CN | 105132570 A | 12/2015 | |
| WO | 1992010501 A1 | 6/1992 | |
| WO | 1998033382 A1 | 8/1998 | |
| WO | 2000008189 A2 | 2/2000 | |
| WO | WO 2019/140351 A1 * | 7/2019 | ............... A01H 5/10 |

OTHER PUBLICATIONS

Zhang et al.,Seedling resistances to rust diseases in international triticale germplasm, 2010, Crop and Pasture Science, vol. 61, pp. 1036-1048, 2010.*
Ellis et al., Structure, function and evolution of plant disease resistance genes, 2000, Current Opinion in Plant Biology, vol. 3(4), pp. 278-284 (Year: 2000).*
Milanesi, L., 2017, A0A9ROYXK3_TRITD (Year: 2017).*
Milanesi, L., 2019, GenBank: VAI63620.1 (Year: 2019).*
Narusaka et al., Breaking restricted taxonomic functionality by dual resistance genes, 2013, Plant Signaling Behavior, pp. 1-3 (Year: 2013).*
Mcdowell et al., Plant disease resistance genes: recent insights and potential applications, 2003, Trends in Biotechnology, vol. 21( 4), pp. 178-183 (Year: 2003).*
Australian Patent Office, International Search Report and Written Opinion for International Patent Application No. PCT/IB2021/000608, Nov. 30, 2021.
China National Intellectual Property Administration; Office Action and Search Report for CN Application No. 202180075248.2, May 9, 2024.
Steuernagel et al., "Rapid cloning of disease-resistance genes in plants using mutagenesis and sequence capture", Nature Biotechnology, vol. 34, No. 6, pp. 1-7, Apr. 25, 2016.
Zhang et al., "Triticum aestivum haplotype S1 Sr13 (Sr13) gene, complete cds", GenBank Database, Accession No. KY825227, Oct. 2, 2017.
Mishina et al., "Triticum aestivum mRNA, clone: tplb0044e19, cultivar Chinese Spring", GenBank Database, Accession No. AK447990, Oct. 4, 2017.
Wu et al., "Characterization of Wheat Monogenic Lines with Known Sr Genes and Wheat Lines with Resistance to the Ug99 Race Group for Resistance to Prevalent Races of *Puccinia graminis* f. sp. tritici in China", Plant Disease, vol. 104, No. 7, pp. 1939-1943, Jul. 31, 2020.

(Continued)

*Primary Examiner* — Amjad Abraham
*Assistant Examiner* — Christina L Meadows
(74) *Attorney, Agent, or Firm* — Williams Mullen; David M. Saravitz

(57) ABSTRACT

Compositions and methods for enhancing the resistance of plants, particularly wheat and triticale plants to stem rust caused by *Puccinia graminis* f. sp. *tritici* are provided. The compositions comprise nucleic acid molecules encoding resistance (R) gene products and variants thereof and plants, seeds, and plant cells comprising such nucleic acid molecules. The methods for enhancing the resistance of a plant to stem rust comprise introducing a nucleic acid molecule encoding an R gene product into a plant cell. Additionally provided are methods for using the resistant plants in agriculture to limit stem rust.

9 Claims, 10 Drawing Sheets

Specification includes a Sequence Listing.

(56) References Cited

OTHER PUBLICATIONS

Marais et al. "The derivation of compensating translocations involving homoeologous group 3 chromosomes of wheat and rye." Euphytica, vol. 79(1), pp. 75-80, 1994.

Mcintosh et al. "Wheat rusts: an atlas of resistance genes," CSIRO publishing, title and p. 124, 1995.

Reddy et al. "Transfer of Secale cereale derived Sr27 into Indian wheat cv. Unnath Kalyan Sona." Crop Research, vol. 8(2), pp. 305-307, 1994 (title and abstract only).

Upadhyaya et al. "Genomics accelerated isolation of a new stem rust avirulence gene-wheat resistance gene pair", Nature Plants, vol. 7(9), pp. 1220-1228, Sep. 2021.

Upadhyaya et al. "Comparative genomics of Australian isolates of the wheat stem rust pathogen *Puccinia graminis* f. sp. tritici reveals extensive polymorphism in candidate effector genes", Front. Plant Sci., vol. 5, Article 759, pp. 1-13, Jan. 2015.

W. Zhang et al; "Identification and characterization of Sr13, a tetraploid wheat gene that confers resistance to the Ug99 stem rust race group;" PNAS; pp. E9483-E9492; Oct. 23, 2017.

* cited by examiner

Expected amplicon sizes

|          | 21-0   | 34-2-12 |
|----------|--------|---------|
| P423/A24 | 601bp  | -ve     |
| P423/A26 | -ve    | 531bp   |
| P383/351 | 380bp  | 380bp   |

AvrSr27-1   MHYTPIILMSIGQFLGILIGAGGIVGAMTPHHQSNCNSPSLTFPRFI   48
AvrSr27-2   .............K...MI...S...............C.V.VT.T

AvrSr27-1   GKCDSCQLHTKATNLVSCTSCNKSSLVYEECSTKGCPANWHKSTCQEP   96
AvrSr27-2   K......FN..F...M...V...................

AvrSr27-1   KFNRGILSCYCENCQQHTKEKQTISCKNCKNSATTFSHCSSPFCHSRN   144
AvrSr27-2   ..E..V.HSL.A...K...ATP...........S.YPY......R..

FIG. 6

STEM RUST RESISTANCE GENE

CROSS-REFERENCE TO RELATED APPLICATIONS

This application is the U.S. National Stage of International Application PCT/IB2021/000608, filed Sep. 8, 2021, which designates the U.S. and was published by the International Bureau in English on Mar. 17, 2022, and which claims the benefit of U.S. Provisional Patent Application No. 63/076,153, filed Sep. 9, 2020 and U.S. Provisional Patent Application No. 63/127,220, filed Dec. 18, 2020; all of which are hereby incorporated herein in their entirety by reference.

REFERENCE TO A SEQUENCE LISTING SUBMITTED AS A TEXT FILE

The official copy of the sequence listing is submitted electronically via EFS-Web as an ASCII formatted sequence listing with a file named 070294-0193SEQLST.TXT, created on Sep. 7, 2021 and having a size of 44.3 kilobytes, and is filed concurrently with the specification. The sequence listing contained in this ASCII formatted document is part of the specification and is herein incorporated by reference in its entirety.

FIELD OF THE INVENTION

The present invention relates to the fields of gene isolation and plant improvement, particularly to enhancing the resistance of plants to plant disease through the use of disease resistance genes.

BACKGROUND OF THE INVENTION

Plant diseases cause significant yield losses in world-wide wheat production. Among the most damaging diseases of wheat are the rusts. Wheat stem rust caused by *Puccinia graminis* f. sp. *tritici* (Pgt) is one of the most devastating diseases affecting wheat production today. While wheat plants comprising resistance (R) genes against Pgt have proven effective in limiting the agronomic losses caused by wheat stem rust, new races of Pgt have appeared recently for which the R genes are not effective. While pesticides can be used to control wheat stem rust, pesticides are expensive and at odds with the sustainable intensification of agriculture, and in developing countries, pesticides are simply unaffordable for subsistence farmers.

The sustainable intensification of agriculture will require increased use of genetic solutions instead of chemical solutions (e.g. pesticides) to protect crops against pathogens and pests (Jones et al. (2014) *Philos. T Roy. Soc. B* 369: 20130087). However, traditional methods for introducing R genes typically involve long breeding timelines to break linkage to deleterious alleles of other genes. Furthermore, R genes can be overcome within a few seasons when deployed one at a time (McDonald and Linde (2002) *Annu. Rev. Phytopathol.* 40:349-379). Molecular cloning, however, makes it possible to avoid linkage drag and simultaneously introduce multiple R genes (Dangl et al. (2013) *Science* 341:746-751), which should delay resistance-breaking pathogen race evolution and thus, provide more durable resistance (McDonald and Linde (2002) *Annu. Rev. Phytopathol.* 40:349-379).

BRIEF SUMMARY OF THE INVENTION

The present invention provides nucleic acid molecules for resistance (R) genes that are known to confer upon a plant resistance to at least one race of the pathogen that causes wheat stem rust, *Puccinia graminis* f sp. *tritici* (Pgt). In one embodiment, the present invention provides nucleic acid molecules comprising the R gene, Sr27, and variants thereof including, for example, orthologs and non-naturally occurring variants.

The present invention further provides plants, plant cells, and seeds comprising in their genomes one or more polynucleotide constructs of the invention. The polynucleotide constructs comprise a nucleotide sequence encoding a resistance (R) protein of the present invention. Such R proteins are encoded by the R genes of the present invention. In a preferred embodiment, the plants and seeds are transgenic wheat plants and seeds that have been transformed with one or more polynucleotide constructs of the invention. Preferably, such wheat plants comprise enhanced resistance to at least one race of the pathogen that causes wheat stem rust, Pgt, when compared to the resistance of a control wheat plant that does not comprise the polynucleotide construct.

The present invention provides methods for enhancing the resistance of a plant, particularly a wheat or triticale plant, to stem rust caused by Pgt. Such methods comprise introducing into at least one plant cell a polynucleotide construct comprising a nucleotide sequence of an R gene of the present invention. In some embodiments, the polynucleotide construct or part thereof is stably incorporated into the genome of the plant cell, and in other embodiments, the polynucleotide construct is not stably incorporated into the genome of the plant cell. The methods for enhancing the resistance of a plant to stem rust can optionally further comprise regenerating the plant cell into a plant that comprises in its genome the polynucleotide construct. Preferably, such a plant comprises enhanced resistance to stem rust caused by at least one race of Pgt, relative to a control plant.

The present invention additionally provides methods for identifying a plant, particularly a wheat or triticale plant, that displays newly conferred or enhanced resistance to stem rust caused by Pgt. The methods comprise detecting in the plant the presence of at least one R gene of the present invention, particularly Sr27.

Methods of using the plants of the present invention in agricultural crop production to limit stem rust caused by Pgt are also provided. The methods comprise planting a seed produced by a plant of the present invention, wherein the seed comprises at least one R gene nucleotide sequence of the present invention. The methods further comprise growing a plant under conditions favorable for the growth and development of the plant, and optionally harvesting at least one seed or plant part from the plant.

Additionally provided are plants, plant parts, seeds, plant cells, other host cells, expression cassettes, and vectors comprising one or more of the nucleic acid molecules of the present invention.

BRIEF DESCRIPTION OF THE DRAWINGS

FIG. 5A is a schematic diagram of the positions and sizes (in kbp) of deletions in six Sr27-virulent isolates from Australia (34-2, 12 and 34-2,12,13) and South Africa (SA03, SA05, SA06, SA07) indicated relative to chromosome 2B (grey bar). Deletions were detected by read mapping of Illumina DNA sequence reads from these isolates onto the Pgt21-0 genome sequence. The positions of primers P423, P424 and P426 on chromosome 2B around the AvrSr27 locus are indicated (arrow heads) relative to the boundaries of the deletion region in 34-2-12. FIG. 5B shows confirmation of the 13 Kbp deletion in Sr27-virulent rust isolate 34-2-12. PCR amplification products from genomic DNA of Pgt21-0 and 34-2,12 are shown after separation on a 1% agarose gel. The primers P383 and P351 are designed to amplify a fragment of the AvrSr50 gene as a control region that is identical in both isolates.

FIG. 6 is an amino acid sequence alignment of two related secreted AvrSr27 protein variants from Pgt21-0 that are encoded by the AvrSr27 locus. AvrSr27-1 (SEQ ID NO: 6) and AvrSr27-2 (SEQ ID NO: 8) are encoded at the avirulence allele on chromosome 2B. The amino acid sequence (single letter code) of AvrSr27-1 is shown with identical residues in other variants indicated by a '.'. The predicted signal peptide region is underlined and in bold.

SEQUENCE LISTING

Figure 1:
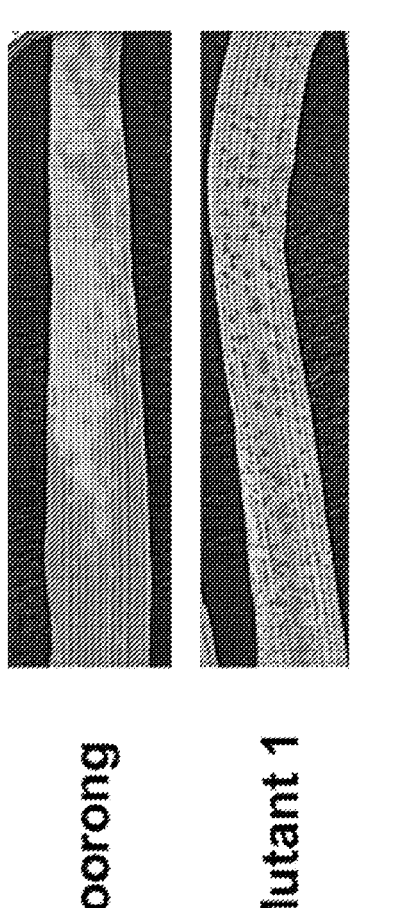
FIG. 1 is a photographic illustration of the identification of a Sr27 susceptible mutant. Coorong (top panel) and the EMS-derived susceptible Mutant 1 (bottom panel) were inoculated with Pgt21-0 and photographed 14 days after infection.

The nucleotide and amino acid sequences listed in the accompanying sequence listing, drawings, and those set forth hereinbelow are shown using standard letter abbreviations for nucleotide bases, and either the one-letter or three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence comprising the R gene, Sr27, from triticale (×*Triticosecale* Wittmack) cv. Coorong. The nucleotide sequence comprises in a 5' to 3' direction: a 5'-untranslated region (5'-UTR) at nucleotides 1-39, protein coding region 40-872, an intron at nucleotides 873-1779, protein coding region at nucleotides 1780-3814, a TGA stop codon at 3815-3817, and a 3'-untranslated region (3'-UTR) at nucleotides 3818-3956.

SEQ ID NO: 2 sets forth the nucleotide sequence of the coding region of the cDNA of Sr27 (SEQ ID NO: 1). If desired, a stop codon (e.g. TAA, TAG, or TGA) can be operably linked to the 3' end of a nucleic acid molecule comprising or consisting of SEQ ID NO: 2. The native stop codon of this cDNA is TGA.

SEQ ID NO: 3 sets forth the amino acid sequence of the R protein, Sr27, encoded by the R gene, Sr27 (SEQ ID NO: 1).

SEQ ID NO: 4 sets forth the nucleotide sequence of the open reading frame of the Sr27 (SEQ ID NO: 1). This sequence is the portion of the genomic sequence of Sr27 beginning at the first nucleotide of the start codon and ending at the last nucleotide of the stop codon. This sequence contains introns.

SEQ ID NO: 5 sets forth the coding sequence of AvrSr27-1 from *Puccinia graminis* f sp. *tritici* (Pgt) isolate Pgt21-0 with the predicted signal peptide excluded and replaced by a single methionine start codon.

SEQ ID NO: 6 sets forth the amino acid sequence of the Avr27-1 protein encoded by AvrSr27-1 (SEQ ID NO: 5) from Pgt isolate Pgt21-0.

SEQ ID NO: 7 sets forth the coding sequence of AvrSr27-2 from Pgt isolate Pgt21-0 PGT21_006593_AvrSr27-2 with the predicted signal peptide excluded and replaced by a single methionine start codon.

SEQ ID NO: 8 sets forth the amino acid sequence of the Avr27-2 protein encoded by AvrSr27-2 (SEQ ID NO: 7) from Pgt isolate Pgt21-0.

SEQ ID NOS: 9-39 are nucleotide sequences of the primers in Table 2 below (Example 6).

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to the isolation of a plant resistance (R) gene, particularly R gene that confers upon a plant, particularly a wheat or triticale plant, resistance to stem rust caused by *Puccinia graminis* f. sp. *tritici* (Pgt). Most rust resistance genes belong to the nucleotide-binding leucine-rich repeat receptors (NLR) class which are well known as immune receptors in plants. TIR-containing NLR (TNL) and CC-containing NLR (CNL) are two major classes of plant NLR that are defined based on the presence of either a TIR or CC domain at their N-terminus. Most, if not all, NLRs in cereals belong to the CNL class. Nine all stage stem rust resistance genes have been cloned that originate from *T. monococcum* (Sr21, Sr22, and Sr35), the A genome donor of hexaploid bread wheat, *Aegilops tauschii* (Sr33 and Sr45) the D genome donor of hexaploid bread wheat, diploid rye (Sr50) and durum wheat (Sr13) and Sr26 identified from tall wheat grass (*T. ponticum*).

The present invention relates to Sr27, a locus that provides resistance to many important Pgt isolates worldwide including the Ug99 lineage, and which is present in the rye/wheat hybrid cereal triticale (×*Triticosecale*). As disclosed hereinbelow, the inventors used a combined chemical mutagenesis and nucleotide-binding leucine-rich repeat receptor (NLR) resistance gene enrichment sequencing approach to isolate the R gene, Sr27, from a Pgt-resistant, triticale cultivar ('Coorong') that comprises in its genome the Sr27 stem rust resistance gene.

The present invention provides nucleic acid molecules comprising the nucleotide sequences of R genes, particularly the nucleotide sequence of Sr27 and naturally occurring (e.g. orthologs and allelic variants) and synthetic or artificial (i.e. non-naturally occurring) variants thereof. Such nucleotide sequences of R genes, which are also referred to herein as R gene nucleotide sequences, encode R proteins. R gene nucleotide sequences of the invention include, but not limited to, wild-type R genes comprising a native promoter and the 3' adjacent region comprising the coding region, cDNA sequences, and nucleotide sequences comprising only the coding region. Examples of such R gene nucleotide sequences include the nucleotide sequences set forth in SEQ ID NOS: 1, 2, and 4 and variants thereof. In embodiments in which the native R gene promoter is not used to drive the expression of the nucleotide sequence encoding the R protein, a heterologous promoter can be operably linked to a nucleotide sequence encoding an R protein of the invention to drive the expression of nucleotide sequence encoding an R protein in a plant.

Preferably, the R proteins of the invention are functional R proteins that are capable of conferring to a plant comprising the R protein enhanced resistance to stem rust caused by at least one race of Pgt. In certain embodiments, the R proteins of the present invention comprise broad-spectrum resistance to multiple races of Pgt such as, for example, the R protein encoded by Sr27.

The present invention further provides transgenic plants comprising a polynucleotide construct which comprise an R gene nucleotide sequence of the invention. In some embodiments, the polynucleotide construct is stably incorporated into the genome of the plant, and in other embodiments, the plant is transformed by a transient transformation method and the polynucleotide construct is not stably incorporated into the genome of the plant. Methods for both the stable and transient transformation of plants are disclosed elsewhere herein or otherwise known in the art. In a preferred embodiment of the invention, the transgenic plants are wheat plants that comprise enhanced resistance to stem rust caused by at least one race of Pgt.

In certain embodiments, a transgenic plant of the invention comprises a polynucleotide construct comprising a nucleotide sequence encoding an R protein and a heterologous promoter that is operably linked for expression of the nucleotide sequence encoding an R protein. The choice of heterologous promoter can depend on a number of factors such as, for example, the desired timing, localization, and pattern of expression as well as responsiveness to particular biotic or abiotic stimulus. Promoters of interest include, but are not limited to, pathogen-inducible, constitutive, tissue-preferred, wound-inducible, and chemical-regulated promoters.

In certain embodiments of the invention, the transgenic plant, particularly a transgenic wheat plant, can comprise one, two, three, four, five, six, or more nucleotide sequences encoding an R protein. Typically, but not necessarily, the two or more R proteins will be different from each other. For the present invention, an R protein is different from another R protein when the two R proteins have non-identical amino acid sequences. In certain embodiments of the invention, each of the different R proteins for stem rust has one or more differences in resistance characteristics such as, for example, resistance against a different race and/or group of races of Pgt. It is recognized that by combining two, three, four, five, six, or more nucleotide sequences with each nucleotide sequence encoding a different R protein for wheat stem rust, a wheat plant can be produced that comprises broad spectrum resistance against multiple races of Pgt. Such a wheat plant finds use in agriculture in regions where multiple races of Pgt are known to occur.

Examples of wheat stem rust R genes that can be combined in a single wheat plant with an nucleotide sequence of the present invention include Sr22 (WO 2017/024053), Sr26, Sr32, Sr33 (GenBank Accession No. KF031299.1), Sr35 (GenBank Accession No. KC573058.1), Sr39, Sr40, Sr45 (WO 2017/024053), Sr47, Sr50, SrTA1662 (WO 2019140351), and the adult plant resistance gene Sr57/Lr34 (GenBank Accession No. FJ436983.1) and Sr55/Lr67.

A transgenic plant of the invention comprising multiple R genes can be produced by transforming a plant that already comprises one or more other R gene nucleotide sequences with a polynucleotide construct comprising an R gene nucleotide sequence of the invention including, for example, an Sr27 nucleotide sequence or variant thereof. Such a plant that already comprises one or more other R gene nucleotide sequences can comprise R genes that are native to the genome of the plant, that were introduced into the plant via sexual reproduction, or that were introduced by transforming the plant or a progenitor thereof with an R gene nucleotide sequence. Alternatively, the one or more other R gene nucleotide sequences can be introduced into a transgenic plant of the invention, which already comprises a polynucleotide construct of the invention, by, for example, transformation or sexual reproduction.

In other embodiments, two or more different R gene sequences can be introduced into a plant by stably transforming the plant with a polynucleotide construct or vector comprising two or more R gene nucleotide sequences. It is recognized that such an approach can be preferred for plant breeding as it is expected that the two or more R gene nucleotide sequences will be tightly linked and thus, segregate as a single locus. Alternatively, a polynucleotide construct of the present invention can be incorporated into the genome of a plant in the immediate vicinity of another R gene nucleotide sequence using homologous recombination-based genome modification methods that are described elsewhere herein or otherwise known in the art.

The present invention further provides methods for enhancing the resistance of a plant, particularly a wheat or triticale plant, to stem rust caused by Pgt. The methods comprise introducing a polynucleotide construct of the invention into at least one plant cell. In certain embodiments, the polynucleotide construct is stably incorporated into the genome of a plant cell. If desired, the methods can further comprise regenerating the plant cell into a plant comprising in its genome the polynucleotide construct. Preferably, such a regenerated plant comprises enhanced resistance to stem rust caused by at least one race of Pgt, relative to the resistance of a control plant to stem rust caused by the same race or races of Pgt. If desired, the methods can further comprise producing a plant, as described above, comprising one, two, three, four, five, six, or more nucleotide sequences encoding an R protein, preferably each nucleotide sequence encoding a different R protein.

The plants disclosed herein find use in methods for limiting stem rust caused by Pgt in agricultural crop production, particularly in regions where stem rust is prevalent. The methods of the invention comprise planting a seed produced by a plant of the present invention, wherein the seed comprises at least one R gene nucleotide sequence of the present invention. The methods further comprise growing a plant under conditions favorable for the growth and development of the plant therefrom, and optionally harvesting at least one seed, or other plant part or parts, from the plant.

The present invention additionally provides methods for identifying a plant, particularly a wheat or triticale plant, that displays newly conferred or enhanced resistance to stem rust caused by Pgt. The methods find use in breeding plants for resistance to stem rust. Such resistant plants find use in the agricultural production of wheat seeds. The methods comprise detecting in a plant the presence of at least one R gene of the present invention, particularly Sr27. In some embodiments of the invention, detecting the presence of the R gene comprises detecting the entire R gene in genomic DNA isolated from the plant. In preferred embodiments, however, detecting the presence of an R gene comprises detecting the presence of at least one marker within the R gene. In other embodiments of the invention, detecting the presence of an R gene comprises detecting the presence of the R protein encoded by the R gene using, for example, immunological detection methods involving antibodies specific to the R protein.

In the methods for identifying a plant that displays newly conferred or enhanced resistance to stem rust caused by Pgt, detecting the presence of the R gene in the plant can involve one or more of the following molecular biology techniques that are disclosed elsewhere herein or otherwise known in the art including, but not limited to, isolating genomic DNA and/or RNA from the wheat plant, amplifying nucleic acid molecules comprising the R gene and/or marker therein by PCR amplification, sequencing nucleic acid molecules comprising the R gene and/or marker, identifying the R gene, the marker, or a transcript of the R gene by nucleic acid hybridization, and conducting an immunological assay for the detection of the R protein encoded by the R gene. It is recognized that oligonucleotide probes and PCR primers can be designed to identify the R genes of the present invention and that such probes and PCR primers can be utilized in methods disclosed elsewhere herein or otherwise known in the art to rapidly identify in a population of plants one or more plants comprising the presence of an R gene of the present invention. It is further recognized that detecting the presence of the R gene can involve detecting the presence of a fragment of the R gene of the present invention. Such a fragment of an R gene of the present invention can comprise, for example, at least 10, 20, 50, 75, 100, 125, 150, 175, 200, 300, 400, 500, 600, 700, 800, 900, 1000, 1500, 2000, 2500, 3000, 3500, or more contiguous nucleotides.

Depending on the desired outcome, the polynucleotide constructs of the invention can be stably incorporated into the genome of the plant cell or not stably incorporated into the genome of the plant cell. If, for example, the desired outcome is to produce a stably transformed plant with enhanced resistance to wheat stem rust caused by at least one race of Pgt, then the polynucleotide construct can be, for example, fused into a plant transformation vector suitable for the stable incorporation of the polynucleotide construct into the genome of the plant cell. Typically, the stably transformed plant cell will be regenerated into a transformed plant that comprises in its genome the polynucleotide construct. Such a stably transformed plant is capable of transmitting the polynucleotide construct to progeny plants in subsequent generations via sexual and/or asexual reproduction. Plant transformation vectors, methods for stably transforming plants with an introduced polynucleotide construct and methods for plant regeneration from transformed plant cells and tissues are generally known in the art for both monocotyledonous and dicotyledonous plants or described elsewhere herein.

The present invention provides nucleic acid molecules comprising R genes. Preferably, the R genes are capable of conferring upon a host plant, particularly a wheat or triticale plant, enhanced resistance to at least one race of the pathogen that causes stem rust, Pgt. More preferably, the R genes are capable of conferring upon a host plant, particularly a wheat or triticale plant, enhanced resistance to two, three, four, or more races of Pgt. Thus, such R genes find use in limiting stem rust caused by Pgt in agricultural production. The R genes of the present invention include, but are not limited to, the R genes whose nucleotide sequences are disclosed herein but also include orthologs and other variants that are capable of conferring to a plant resistance to stem rust caused by at least one race of Pgt. Methods are known in the art or otherwise disclosed herein for determining resistance of a plant to stem rust caused by at least one race of Pgt.

The methods of the present invention find use in producing plants, particularly wheat and triticale plants, with enhanced resistance to stem rust caused by at least one race of Pgt. Typically, the methods of the present invention will enhance or increase the resistance of the subject plant to one race of Pgt by at least 25%, 50%, 75%, 100%, 150%, 200%, 250%, 500% or more when compared to the resistance of a control plant to the same race or races of Pgt. Unless stated otherwise or apparent from the context of a use, a control plant for the present invention is a plant that does not comprise the polynucleotide construct of the present invention. Preferably, the control plant is essentially identical (e.g. same species, subspecies, and variety) to the plant comprising the polynucleotide construction of the present invention except the control does not comprise the polynucleotide construct. In some embodiments, the control will comprise a polynucleotide construct but not comprise the one or more R gene sequences that are in a polynucleotide construct of the present invention.

Additionally, the present invention provides transformed plants, seeds, and plant cells produced by the methods of present invention and/or comprising a polynucleotide construct of the present invention. Also provided are progeny plants and seeds thereof comprising a polynucleotide construct of the present invention. The present invention also provides seeds, vegetative parts, and other plant parts produced by the transformed plants and/or progeny plants of the invention as well as food products and other agricultural products produced from such plant parts that are intended to be consumed or used by humans and other animals including, but not limited to pets (e.g., dogs and cats) and livestock (e.g., pigs, cows, chickens, turkeys, and ducks).

The methods of the invention can be used to enhance the resistance of a plant, particularly a wheat or triticale plant, to stem rust, particularly stem rust caused by at least one race of Pgt. As used herein, the term "wheat plant" generally refers to a plant that is a member of the *Triticum* genus or a member of another genus within the *Triticeae* tribe, particularly a member of another genus that is capable of producing interspecific hybrids with at least one *Triticum* sp. Examples of such another genus within the *Triticeae* tribe are *Aegilops* and *Secale*.

The wheat plants of the present invention include, for example, domesticated and non-domesticated plants. The wheat plants of the present invention include, but are not limited to, the following *Triticum, Aegilops* and *Secale* species: *T. aestivum, T. monococcum, T. turgidum, T. boeoticum, T. timopheevii,* and *T. urartu, Aegilops tauschii, Secale cereale,* and hybrids thereof. Examples of *T. aestivum* subspecies included within the present invention are *aestivum* (common wheat), *compactum* (club wheat), *macha (macha* wheat), *vavilovi (vavilovi* wheat), *spelta,* and sphaerococcum (shot wheat). Examples of *T. turgidum* subspecies included within the present invention are *turgidum, carthlicum,* dicoccom, durum, paleocoichicum, *polonicum, turanicum,* and *dicoccoides.* Examples of *T. monococcum* subspecies included within the present invention are *monococcum* (einkorn) and aegilopoides. In one embodiment of the present invention, the wheat plant is a member of the *Triticum turgidum* species; and in particular, a member of the Durum subspecies, for example, a Ciccio, Colosseo, or Utopia cultivar. It is recognized that a wheat plant of the present invention can be a domesticated wheat plant or a non-domesticated wheat plant.

The present invention also encompasses triticale plants, triticale plant parts, and triticale plant cells comprising an R gene of the invention. As used herein, a "triticale plant" refers to a plant that is created by crossing a rye plant (*Secale cereale*) with either a tetraploid wheat plant (e.g. *Triticum turgidum*) or a hexaploid wheat plant (e.g. *Triticum aestivum*). The present invention also includes seeds produced by the triticale plants described herein and methods for controlling weeds in the vicinity of the triticale plants described herein. As used herein, the term "wheat plant"

encompasses triticale plants unless stated otherwise or apparent from the context of use.

The term "plant" is intended to encompass plants at any stage of maturity or development, as well as any tissues or organs (plant parts) taken or derived from any such plant unless otherwise clearly indicated by context. As used herein, the term "plant" includes, but is not limited to, seeds, plant cells, plant protoplasts, plant cell tissue cultures from which plants can be regenerated, plant calli, plant clumps, and plant cells that are intact in plants or parts of plants such as embryos, pollen, ovules, seeds, tubers, propagules, leaves, flowers, branches, fruits, roots, root tips, anthers, and the like. The present invention also includes seeds produced by the plants of the present invention.

Progeny, variants, and mutants of the regenerated plants are also included within the scope of the invention, provided that these parts comprise the introduced polynucleotides. As used herein, "progeny" and "progeny plant" comprise any subsequent generation of a plant whether resulting from sexual reproduction and/or asexual propagation, unless it is expressly stated otherwise or is apparent from the context of usage.

Plant parts include, but are not limited to, seeds, stems, roots, flowers, ovules, stamens, leaves, embryos, meristematic regions, callus tissue, anther cultures, gametophytes, sporophytes, pollen, microspores, protoplasts, and the like.

In one embodiment of the invention, the nucleotide sequences encoding R proteins have at least about 80%, 85%, 90%, 91%, 92%, 93%, 94%, 95%, 96%, 97%, 98%, 99% or more sequence identity to the entire nucleotide sequence set forth in SEQ ID NO: 1, 2, and/or 4, or to a fragment thereof.

The present invention encompasses isolated or substantially purified polynucleotide (also referred to herein as "nucleic acid molecule", "nucleic acid" and the like) or protein (also referred to herein as "polypeptide") compositions including, for example, polynucleotides and proteins comprising the sequences set forth in the accompanying Sequence Listing as well as variants and fragments of such polynucleotides and proteins. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" it is intended a portion of the polynucleotide or a portion of the amino acid sequence and hence protein encoded thereby. Fragments of polynucleotides comprising coding sequences may encode protein fragments that retain biological activity of the full-length or native protein. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

Polynucleotides that are fragments of a native R polynucleotide comprise at least 16, 20, 50, 75, 100, 125, 150, 175, 200, 300, 400, 500, 1000, 1500, 2000, 2500, 3000, or 3500 contiguous nucleotides, or up to the number of nucleotides present in a full-length R polynucleotide disclosed herein.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the R proteins of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode an R protein of the invention. Generally, variants of a particular polynucleotide of the invention will have at least about 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. In certain embodiments of the invention, variants of a particular polynucleotide of the invention will have at least about 80%, 85%, 90%, 91%, 92%, 93%, 94%, 95%, 96%, 97%, 98%, 99% or more sequence identity to at least one nucleotide sequence selected from the group consisting of SEQ ID NOS: 1, 2, and 4, and optionally comprises a non-naturally occurring nucleotide sequence that differs from the nucleotide sequence set forth in SEQ ID NO: 1, 2, and/or 4 by at least one nucleotide modification selected from the group consisting of the substitution of at least one nucleotide, the addition of at least one nucleotide, and the deletion of at least one nucleotide.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptide of SEQ ID NO: 3 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 80%, 85%, 86%, 87%, 88%, 89%, 90%, 91%, 92%, 93%, 94%, 95%, 96%, 97%, 98%, 99% or more sequence identity. In certain embodiments of the invention, variants of a particular polypeptide of the invention will have at least about 80%, 85%, 90%, 91%, 92%, 93%, 94%, 95%, 96%, 97%, 98%, 99% or more sequence identity to the amino acid sequence set forth SEQ ID NO: 3, and optionally comprises a non-naturally occurring amino acid sequence that differs from the amino acid set forth in SEQ ID NO: 3 by at least one amino acid modification selected from the group consisting of the substitution of at least one amino acid, the addition of at least one amino acid, and the deletion of at least one amino acid.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Such variants may result from, for example, genetic polymorphism or from human manipulation. Biologically active variants of an R protein will have at least about 80%, 85%, 86%, 87%, 88%, 89%, 90%, 91%, 92%, 93%, 94%, 95%, 96%, 97%, 98%, 99% or more sequence identity to the amino acid sequence for the native protein (e.g. the amino acid sequence set forth in SEQ ID NO: 3) as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. Methods for mutagenesis and polynucleotide alterations are well known in the art. See, for example, Kunkel (1985) *PNAS* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant and other variant forms. Likewise, the proteins of the invention encompass both naturally occurring proteins as well as variations and modified forms thereof. More preferably, such variants confer to a plant or part thereof comprising the variant enhanced resistance stem rust caused by at least one race of Pgt. In some embodiments, the mutations that will be made in the DNA encoding the variant will not place the sequence out of reading frame. Optimally, the mutations will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that are disclosed herein below.

For example, a wheat plant that is susceptible to wheat stem rust caused by a particular race of Pgt can be transformed with an Sr27 polynucleotide, regenerated into a transformed or transgenic plant comprising the polynucleotide, and tested for resistance to wheat stem rust caused by the particular race of Pgt using standard resistance assays known in the art or described elsewhere herein. Preferred variant polynucleotides and polypeptides of the present invention confer or are capable of conferring upon a wheat plant enhanced resistance to at least one race of Pgt that is known to cause wheat stem rust in a susceptible wheat plant.

Variant polynucleotides and proteins also encompass sequences and proteins derived from a mutagenic and recombinogenic procedure such as DNA shuffling. Strategies for such DNA shuffling are known in the art. See, for example, Stemmer (1994) *PNAS* 91:10747-10751; Stemmer (1994) *Nature* 370:389-391; Crameri et al. (1997) *Nature Biotech.* 15:436-438; Moore et al. (1997) *J Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 80%, 85%, 86%, 87%, 88%, 89%, 90%, 91%, 92%, 93%, 94%, 95%, 96%, 97%, 98%, 99%, or greater sequence identity. Functions of orthologs are often highly conserved among species. Thus, isolated polynucleotides that encode R proteins and which hybridize under stringent conditions to at least one of the R proteins disclosed herein or otherwise known in the art, or to variants or fragments thereof, are encompassed by the present invention.

In one embodiment, the orthologs of the present invention have coding sequences comprising at least 80%, 85%, 86%, 87%, 88%, 89%, 90%, 91%, 92%, 93%, 94%, 95%, 96%, 97%, 98%, 99%, or greater nucleotide sequence identity to a nucleotide sequence selected from the group consisting of the nucleotide sequences set forth in SEQ ID NOS: 1, 2, and 4, and/or encode proteins comprising at least 80%, 85%, 86%, 87%, 88%, 89%, 90%, 91%, 92%, 93%, 94%, 95%, 96%, 97%, 98%, 99%, or greater amino acid sequence identity to the amino acid sequence set forth in SEQ ID NO: 3.

Like other NLR proteins, the Sr27 protein comprises certain conserved domains. In Sr27 (comprising the amino acid sequence set forth in SEQ ID NO: 3), the conserved domains include, for example, a coiled-coil domain (amino acids 9 to 160), a nucleotide-binding domain (amino acids 173 to 520) and a leucine-rich repeat domain (amino acids 530 to 940). Preferably, variant Sr27 proteins of the present invention comprise a coiled-coil domain, a nucleotide-binding domain, and a leucine-rich repeat domain corresponding to the domains of Sr27 set forth above.

In some embodiments, variant Sr27 proteins of the present invention comprise a higher percentage of amino acid sequence identity to one, two, or three of such conserved domains than to the full-length amino acid sequence of the Sr27 (SEQ ID NO: 3) or protein disclosed herein. Preferably, such variants comprise a corresponding domain or domains having at least 94%, 95%, 96%, 97%, 98%, 99%, or 100% sequence identity to one, two, or three of the domains of Sr27 set forth above and further comprise an amino acid sequence having at least 91%, 92%, 93%, 94%, 95%, 96%, 97%, 98%, or 99% identity to the amino acid sequence set forth in SEQ ID NO: 3.

It is recognized that domains in variant Sr27 proteins corresponding to those conserved domains of Sr27 set forth above, as well as any particular conserved amino acids therein, can be identified by methods known to those of skill in the art or disclosed elsewhere herein such as, for example, multiple sequence alignment. It is further recognized that the positions of such conserved domains and conserved amino acids within a particular variant Sr27 protein can vary from the positions in the amino acid sequence set forth in SEQ ID NO: 3 and that through methods such as, for example, multiple sequence alignment, the corresponding positions of such conserved domains and conserved amino acids can be determined for any variant Sr27 protein of the present invention.

Preferably, the variant Sr27 proteins of the present invention and the polynucleotides encoding them confer, or are capable of conferring upon a wheat plant comprising such a protein and/or polynucleotide, enhanced resistance to at least one race of Pgt that is known to cause wheat stem rust in a susceptible wheat plant.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

It is recognized that the R protein coding sequences of the present invention encompass polynucleotide molecules comprising a nucleotide sequence that is sufficiently identical to the nucleotide sequence of any one or more of SEQ ID NOS: 1, 2, and 4. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 80% or 85% identity, preferably 90% or 91% identity, more preferably 92%, 93%, 94%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) PNAS 87:2264, modified as in Karlin and Altschul (1993) *PNAS* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST; available on the world-wide web at ncbi.nlm.nih.gov). Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, MD, USA) using the default parameters; or any equivalent program thereof. By "equivalent program", it is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the world-wide web at: ebi.ac.uk/Tools/clustalw/index.html).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide constructs comprising R protein coding regions can be provided in expression cassettes for expression in the plant or other organism or non-human host cell of interest. The cassette will include 5' and 3' regulatory sequences operably linked to the R protein coding region. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the R protein coding region to be under the transcriptional regulation of the regulatory regions. The expression cassette may additionally contain selectable marker genes.

The expression cassette will include in the 5'-3' direction of transcription, a transcriptional and translational initiation region (i.e., a promoter), a R protein coding region of the invention, and a transcriptional and translational termination region (i.e., termination region) functional in plants or other organism or non-human host cell. The regulatory regions (i.e., promoters, transcriptional regulatory regions, and translational termination regions) and/or the R protein coding region or of the invention may be native/analogous to the host cell or to each other. Alternatively, the regulatory regions and/or the R protein coding region of the invention may be heterologous to the host cell or to each other.

As used herein, "heterologous" in reference to a nucleic acid molecule or nucleotide sequence is a nucleic acid molecule or nucleotide sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The present invention provides host cells comprising at least one of the nucleic acid molecules, expression cassettes, and vectors of the present invention. In preferred embodiments of the invention, a host cell is a plant cell. In other embodiments, a host cell is selected from the group consisting of a bacterium, a fungal cell, and an animal cell. In certain embodiments, a host cell is a non-human animal cell. However, in some other embodiments, the host cell is an in-vitro cultured human cell. In yet some other embodiments, the host cell is a microorganism, particularly a unicellular microorganism. Microorganisms include, but are not limited to, archaebacteria, eubacteria, yeasts, and algae.

While it may be optimal to express the R protein using heterologous promoters, the native promoter of the corresponding R gene may be used.

The termination region may be native with the transcriptional initiation region, may be native with the operably linked R protein coding region of interest, may be native with the plant host, or may be derived from another source (i.e., foreign or heterologous to the promoter, the R protein of interest, and/or the plant host), or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nuc. Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the R protein coding sequences within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997)*Mol. Gen Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *PNAS* 90(20):9586-9590; and Guevara-Garcia et al. (1993) *Plant* 4(3):495-505. Such promoters can be modified, if necessary, for weak expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *PNAS* 83:2427-2430; Somsisch et al. (1988) *Mot Gen. Genet.* 2:93-98; and Yang (1996) *PNAS* 93:14972-14977. See also, Chen et al. (1996) *Plant J* 10:955-966; Zhang et al. (1994) *PNAS* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Also of interest are the native promoters from other resistance genes from the target species. These promoters are often pathogen-inducible, and are likely to express the resistance gene at appropriate levels and in appropriate tissues. Examples of such promoters are the Sr57/Lr34, Sr33, Sr35, and Sr22 promoters of wheat (Risk et al. (2012) *Plant Biotechnol J* 10: 447-487; Periyannan et al. (2013) *Science* 341: 786-788; Saintenac et al. (2013) *Science* 341: 783-786; Steuernagel et al. (2016) *Nature Biotechnol.* 34(6): 652-655, doi: 10.1038/nbt.3543).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *PNAS* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *PNAS* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *PNAS* 86:5400-5404; Fuerst et al. (1989) *PNAS* 86:2549-2553; Deuschle et al. (1990) *Science* 248:480-483; Gossen (1993) Ph.D. Thesis, University of Heidelberg; Reines et al. (1993) *PNAS* 90:1917-1921; Labow et al. (1990) *Mol. Cell. Biol.* 10:3343-3356; Zambretti et al. (1992) *PNAS* 89:3952-3956; Bairn et al. (1991) *PNAS* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *PNAS* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not intended to be limiting. Any selectable marker gene can be used in the present invention.

Numerous plant transformation vectors and methods for transforming plants are available. See, for example, An et al. (1986) *Plant Physiol.*, 81:301-305; Fry et al. (1987) *Plant Cell Rep.* 6:321-325; Block (1988) *Theor. Appl. Genet.* 76:767-774; Hinchee et al. (1990) *Stadler Genet. Symp.* 203212.203-212; Cousins, et al. (1991) *Aust. J. Plant Physiol.* 18:481-494; Chee and Slightom (1992) *Gene.*118: 255-260; Christou et al. (1992) *Trends Biotechnol.* 10:239-246; D'Halluin et al. (1992) *Bio/Technol.* 10:309-314; Dhir et al. (1992) *Plant Physiol.* 99:81-88; Casas et al. (1993) *PNAS* 90:11212-11216; Christou (1993) *In Vitro Cell. Dev. Biol.-Plant;* 29P:119-124; Davies et al. (1993) *Plant Cell Rep.* 12:180-183; Dongand Mchughen (1993) *Plant Sci.* 91:139-148; Franklin et al. (1993) *Plant Cell Rep.* 12(2): 74-79, doi: 10.1007/BF00241938; Golovkin et al. (1993) *Plant Sci.* 90:41-52; Asano et al. (1994) *Plant Cell Rep.* 13; *Ayeres and Park* (1994) *Crit. Rev. Plant Sci.* 13:219-239; Barcelo et al. (1994) *Plant J.* 5:583-592; Becker et al. (1994) *Plant J.* 5:299-307; Borkowska et al. (1994) *Acta Physiol. Plant* 16:225-230; Christou (1994) *Agro. Food Ind. Hi Tech.* 5: 17-27; Eapen et al. (1994) *Plant Cell Rep.* 13:582-586; Hartman, et al. (1994) *Bio-Technology* 12: 919923; Ritala et al. (1994) *Plant Mol. Biol.* 24:317-325; and Wan and Lemaux (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *PNAS* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et al. (1988) *Biotechnology* 6:923-926); and Lecl transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *PNAS* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *PNAS* 84:5345-5349 (Liliaceae); De Wet et al. (1985) in The Experimental Manipulation of Ovule Tissues, ed. Chapman et al. (Longman, New York), pp. 197-209 (pollen); Kaeppler et al. (1990) *Plant Cell Reports* 9:415-

418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

If desired, the modified viruses or modified viral nucleic acids can be prepared in formulations. Such formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al. Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, antifreezing agents, for seed treatment formulation also optionally colorants and/or binders and/or gelling agents.

In specific embodiments, the polynucleotide constructs and expression cassettes of the invention can be provided to a plant using a variety of transient transformation methods known in the art. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *PNAS Sci.* 91: 2176-2180 and Hush et al. (1994) *J. Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described elsewhere herein.

The cells that have been transformed may be grown into plants in accordance with conventional ways. See, for example, McCormick et al. (1986) *Plant Cell Reports* 5:81-84. These plants may then be grown, and either pollinated with the same transformed line or different lines, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

In certain embodiments of the invention, the nucleotide sequence of a non-functional allele at an R gene locus of the present invention can be modified in planta to a functional allele that provides resistance to at least one race of a plant pathogen. Thus, the present invention provides methods for producing a plant, particularly a triticale plant, with enhanced resistance to stem rust. The methods comprise modifying in a plant or at least one cell thereof, a non-functional allele of the resistance gene Sr27 so as to make a functional allele, whereby the resistance of the plant to stem rust is enhanced. In preferred embodiments, the plant that is produced is a non-transgenic plant, particularly a non-transgenic triticale plant. The methods can further comprise regenerating the plant cell or plant cells comprising the functional allele into a plant comprising the functional allele.

In one embodiment of the invention, a non-functional allele or susceptible allele that is present at the Sr27 locus in a triticale plant can be modified to a functional allele that provides resistance to, for example, at least one, two, three, or four races of Pgt. In another embodiment of the invention, a non-functional allele that is present at the Sr27 locus in a triticale plant can be modified to a functional allele that provides resistance to at least one, two, three, or four races of Pgt that cause stem rust. For example, a non-functional allele at the Sr27 locus can be modified to form whereby the modified allele comprises the nucleotide sequence of Sr27 set forth in SEQ ID NO: 1 and/or a nucleotide sequence encoding the amino sequence set forth SEQ ID NO: 3.

Any methods known in the art for modifying DNA in the genome of a plant can be used to modify the nucleotide sequences of an R gene in planta, e.g. to modify the nucleotide sequence of a non-functional allele to that of a functional allele that provides resistance to a plant pathogen. Such modifications to the DNA in the genome of a plant include, for example, insertions, deletions, substitutions, and combinations thereof. The insertions, deletions, and substitutions can be made using any method known in the art such as, for example, by genome editing techniques as described elsewhere herein or otherwise known in the art.

The insertions comprise an insertion of at least one nucleotide or base pair (bp) in an allele of an R gene of the present invention. The insertion can comprise insertion of any size DNA fragment into the genome. The inserted DNA can be 1 bp in length, 1-5 bp in length, 5-10 bp in length, 10-15 bp in length, 15-20 bp in length, 20-30 bp in length, 30-50 bp in length, 50-100 bp in length, 100-200 bp in length, 200-300 bp in length, 300-400 bp in length, 400-500 bp in length, 500-600 bp in length, 600-700 bp in length, 700-800 bp in length, 800-900 bp in length, 900-1000 by in length, 1000-1500 bp.

The deletions comprise the deletion of at least one bp from an allele of an R gene of the present invention. As used herein, a "deletion" is meant the removal of one or more nucleotides or base pairs from the DNA. Provided herein, a deletion in an allele of an R gene can be the removal of at least 1, at least 20, at least 50, at least 100, at least 500, at least 1000, at least 5000 or more bp.

The substitutions comprise the replacement of at least one bp from an allele of an R gene of the present invention with another bp. As used herein, a "substitution" is meant the replacement of one or more nucleotides or base pairs from the DNA with non-identical nucleotides or base pairs. When the substitution comprises two or more nucleotides, the two or more nucleotides can be contiguous or non-contiguous within the DNA sequence of the allele. Provided herein, a substitution in an allele of an R gene can be the replacement of at least 1, at least 20, at least 50, at least 100, at least 500, at least 1000, at least 5000 or more base pairs. In some embodiments, the substitution can be the nucleotide sequence of the entire allele or any portion or portions thereof such as, for example, the transcribed region, the 5' untranslated region, the 3' untranslated region, an exon, or an intron.

In certain embodiments of the invention, the modification of a non-functional allele at an R gene locus is a homozygous modification. By "homozygous modification" is meant that the modification is in both alleles of the R gene locus in a particular genome of a plant. In other cases, the modification of the R gene locus gene is heterozygous, that is, the modification is only in one allele of the of the R gene locus in the genome of a plant. It is recognized the plants of the invention include, for example, crop plants with genomes that are diploid or polyploid (e.g. tetraploid or hexaploid), including autopolyploids and allopolyploids. An autopolyploid is an organism having more than two sets of chromosomes, all of which were derived from the same species. An allopolyploid is an organism having two or more complete sets of chromosomes that are derived from different species. Depending on the particular the crop plant, 1, 2, 3, 4, 5, 6 or more alleles at an R gene locus of the plant can be modified using the methods disclosed.

Any methods known in the art for modifying DNA in the genome of a plant can be used to alter the coding sequences of an R gene in planta, e.g. to alter the nucleotide sequence of a homologous susceptible allele to that of an allele that provides resistance to at least one race of stem rust. Such methods known in the art for modifying DNA in the genome of a plant include, for example, mutation breeding and genome editing techniques, such as, for example, methods involving targeted mutagenesis, site-directed integration (SDI), and homologous recombination. Targeted mutagenesis or similar techniques are disclosed in U.S. Pat. Nos. 5,565,350; 5,731,181; 5,756,325; 5,760,012; 5,795,972, 5,871,984, and 8,106,259; all of which are herein incorporated in their entirety by reference. Methods for gene modification or gene replacement comprising homologous recombination can involve inducing single-strand or double-strand breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered endonucleases to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J Mol Biol* 355:443-58; Ashworth et al., (2006) *Nature* 441:656-9; Doyon et al. (2006) *J Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

TAL effector nucleases (TALENs) can be used to make double-strand breaks at specific recognition sequences in the genome of a plant for gene modification or gene replacement through homologous recombination. TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, FoId. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze and Boch (2010) *Virulence* 1:428-432; Christian et al. *Genetics* (2010) 186: 757-761; Li et al. (2010) *Nuc. Acids Res.* (2010) doi: 10.1093/nar/gkq704; and Miller et al. (2011) *Nature Biotechnology* 29:143-148; all of which are herein incorporated by reference.

The CRISPR/Cas nuclease system can also be used to make single-strand or double-strand breaks at specific recognition sequences in the genome of a plant for gene modification or gene replacement through homologous recombination. The CRISPR/Cas nuclease is an RNA-guided (simple guide RNA, sgRNA in short) DNA endonuclease system performing sequence-specific double-stranded breaks in a DNA segment homologous to the designed RNA. It is possible to design the specificity of the sequence (Cho et al. (2013) *Nat. Biotechnol.* 31:230-232; Cong et al. (2013) *Science* 339:819-823; Mali et al. (2013) *Science* 339:823-826; Feng et al. (2013) *Cell Res.* 23(10): 1229-1232).

In addition, a ZFN can be used to make double-strand breaks at specific recognition sequences in the genome of a plant for gene modification or gene replacement through homologous recombination. The Zinc Finger Nuclease (ZFN) is a fusion protein comprising the part of the FokI restriction endonuclease protein responsible for DNA cleavage and a zinc finger protein which recognizes specific, designed genomic sequences and cleaves the double-stranded DNA at those sequences, thereby producing free DNA ends (Urnov F. D. et al., Nat Rev Genet. 11:636-46, 2010; Carroll D., Genetics. 188:773-82, 2011).

Breaking DNA using site specific nucleases, such as, for example, those described herein above, can increase the rate of homologous recombination in the region of the breakage. Thus, coupling of such effectors as described above with nucleases enables the generation of targeted changes in genomes which include additions, deletions, substitutions, and other modifications.

Mutation breeding can also be used in the methods provided herein. Mutation breeding methods can involve, for example, exposing the plants or seeds to a mutagen, particularly a chemical mutagen such as, for example, ethyl methanesulfonate (EMS) and selecting for plants that possess a desired modification in the Sr27 gene. However, other mutagens can be used in the methods disclosed herein including, but not limited to, radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Further details of mutation breeding can be found in "Principals of Cultivar Development" Fehr, 1993 Macmillan Publishing Company the disclosure of which is incorporated herein by reference.

The nucleic acid molecules, expression cassettes, vectors, and polynucleotide constructs of the present invention may be used for transformation of any plant species, including, but not limited to, monocots and dicots. Preferred plants of the present invention are wheat plants. Examples of other plant species of interest include, but are not limited to, peppers (*Capsicum* spp; e.g., *Capsicum annuum, C. baccatum, C. chinense, C. frutescens, C. pubescens,* and the like), tomatoes (*Lycopersicon esculentum*), tobacco (*Nicotiana tabacum*), eggplant (*Solanum melongena*), petunia (*Petunia* spp., e.g., *Petunia* x *hybrida* or *Petunia hybrida*), pea (*Pisum sativum*), bean (*Phaseolus vulgaris*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), soybean (*Glycine max*), teff (*Eragrostis tef*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (Mangifera indica), olive (*Olea europaea*), papaya (*Carica papaya*), cashew (*Anacardium occidentale*), macadamia (*Macadamia integrifolia*), almond (*Prunus* amygdalus), sugar beets (*Beta vulgaris*), sugarcane (*Saccharum* spp.), palms, oats, barley, vegetables, ornamentals, and conifers.

In certain embodiments of the invention, the preferred plants are cereal plants. Such cereal plants of the present invention are grass plants (i.e. Poaceae family) cultivated for the edible components of their grain or kernels (i.e. seeds) including, for example, wheat, triticale, rye, barley, oats, maize, sorghum, millet, and rice. In certain other embodiments of the invention, the preferred plants are cereal plants but not including triticale plants.

In some embodiments of the present invention, a plant cell is transformed with a polynucleotide construct encoding an R protein of the present invention. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide. Examples of polynucleotide constructs and nucleic acid molecules that encode R proteins are described elsewhere herein.

The use of the terms "DNA" or "RNA" herein is not intended to limit the present invention to polynucleotide molecules comprising DNA or RNA. Those of ordinary skill in the art will recognize that the methods and compositions of the invention encompass polynucleotide molecules comprised of deoxyribonucleotides (i.e., DNA), ribonucleotides (i.e., RNA) or combinations of ribonucleotides and deoxyribonucleotides. Such deoxyribonucleotides and ribonucleotides include both naturally occurring molecules and synthetic analogues including, but not limited to, nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The polynucleotide molecules of the invention also encompass all forms of polynucleotide molecules including, but not limited to, single-stranded forms, double-stranded forms, hairpins, stem-and-loop structures, and the like. Furthermore, it is understood by those of ordinary skill in the art that the nucleotide sequences disclosed herein also encompasses the complement of that exemplified nucleotide sequence.

The invention is drawn to compositions and methods for enhancing the resistance of a plant to plant disease, particularly to compositions and methods for enhancing the resistance of a plant to stem rust caused by Pgt. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen are minimized or lessened.

As used herein, a "race" refers to any of a group of laboratory isolates or fungal individuals existing in the field that share a similar virulence phenotype on a range of different resistance gene lines of wheat and are likely derived by clonal reproduction.

As used herein, an "isolate" of Pgt refers to a line of Pgt originally isolated as spores collected from an infected plant in the field or in a laboratory/glasshouse setting. Such an "isolate" is subsequently maintained in pure form by infection and re-isolation of spores from a susceptible plant and storage of said spores.

The present invention encompasses the nucleic acid molecules and polynucleotide constructs disclosed herein or in the accompanying sequence listing and/or drawings including, but not limited to: nucleic acid molecules and polynucleotide constructs comprising the nucleotide sequences set forth in SEQ ID NO: 1, 2, and/or 4; and nucleic acid molecules and polynucleotide constructs encoding a protein comprising the amino acid sequence set forth in SEQ ID NO: 3. The present invention further encompasses plants, plant cells, host cells, and vectors comprising at least one of such nucleic acid molecules and/or polynucleotide constructs, as well as food products produced from such plants and plant parts. Additionally encompassed by the present invention are uses of plants comprising at least one of such polynucleotide constructs in the methods disclosed elsewhere herein such as, for example, methods for enhancing the resistance of a plant to stem rust caused by Pgt and methods of limiting stem rust in agricultural crop production.

The following examples are offered by way of illustration and not by way of limitation.

EXAMPLES

Example 1: Cloning of the Sr27 Stem Rust
Resistance Gene

To clone the Sr27 stem rust resistance gene from triticale cv. Coorong, the inventors utilized the MutRenSeq method (Steuernagel et al. (2016) Nature Biotechnol. 34(6):652-655, doi: 10.1038/nbt.3543; WO 2015/127185; both of which are herein incorporated by reference).

The inventors mutagenized seeds of triticale cv. Coorong with ethyl methanesulfonate-derived (EMS) and identified 27 susceptible ethyl methanesulfonate-derived (EMS) mutants from the Coorong background prepared as described below (FIG. 1). Coorong comprises in its genome the Sr27 stem rust resistance gene and was first released in Australia by the University of Adelaide (Macintosh et al. (1983) Can. J. Plant. Pathol. 5:61-69).

Figure 2:
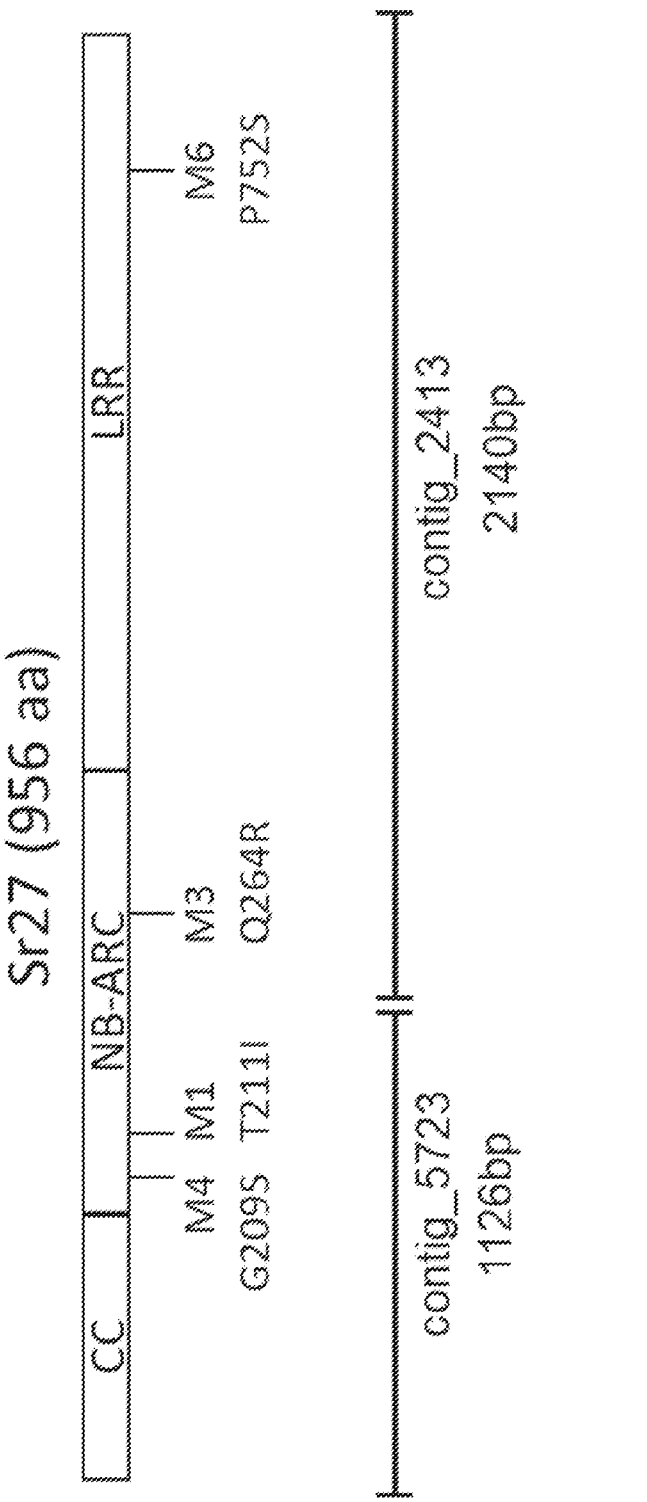
FIG. 2 is a schematic diagram of the Sr27 protein with the amino acid changes in mutants M1, M3, M4 and M6 indicated. Two contigs (#5723 and #2413) assembled from wild-type Coorong after NB-LRR capture and sequencing contain the 5' and 3' regions of this gene. Mutants M1 and M4 contained single base changes in contig 5723 while mutant M6 contained a single base change in contig 2413. The amino acid changes caused by these mutations in the full length Sr27 protein are indicated. Mutant M2 produced no reads specific to these contigs and therefore likely contains a deletion. Mutant M3 was determined by PCR amplification to contain another single nucleotide change in this gene leading to an amino acid change.

NLR-gene capture and sequencing (RenSeq) was performed on wild-type Coorong and four confirmed susceptible mutants (M2, M3, M4 and M6) as described below. Captured reads from wild-type Coorong were assembled and reads from all lines aligned to this reference to identify sequence changes in the mutant lines. One contig (no. 5723) of 1126 base pairs (bp) was found that contained a mutation in three of the four mutants; one (M2) with a full deletion of the sequence and two (M3, M4) with single base changes causing amino acid substitutions Q264R and G209S (in the conserved p-loop) respectively. This contig contained a coiled-coil (CC) domain and p-loop motif, but not the rest of the NB-ARC or LRR domains, suggesting that it represented only part of a full length NLR gene. To identify the remainder of the gene, the contig was aligned to the Triticum aestivum cv. Chinese Spring reference (CSv1) assembly IWGSC RefSeq v1.0 (Appels et al. (2018) Science 361 (6403):eaar7191). The top hit (93.6% identity across the whole DNA sequence) was to the 5'end of a high confidence gene (TraesCS6B01G464400) predicted on chromosome 6B and functionally annotated as a disease resistance gene. The full gene sequence of TraesCS6B01G464400 was then aligned back to the Coorong RenSeq de novo assembly which detected an additional contig (no. 2413) of 2140 bp aligning to the 3' region of this gene with 93.8% identity across the whole sequence. Contig no. 2413 contained both an NB-ARC and LRR domain. Inspection of the read alignments from the mutant Coorong lines confirmed that Contig no. 2413 was also deleted in mutant M2 and identified an additional single base change in mutant M6 (FIG. 2). PCR amplification confirmed that these two contigs were derived from the same gene in wild-type Coorong which encodes a full-length protein of 956 amino acids that contains a coiled-coil (CC) domain at the N-terminus, followed by the NB-ARC domain and then the LRR motifs at the C-terminus (FIG. 2). Amplification from the four mutants confirmed the nucleotide changes detected by RenSeq in each line. Four additional mutants were also examined by PCR amplification and one (M3) contained a single amino acid change (T211I) in the p-loop motif while the gene sequence failed to amplify from the other three (M7, M8, M9) indicating that they contained deletions of this region. The eight independent mutants containing deletions or amino acid changes in this gene provided strong evidence that it confers Sr27 resistance.

Materials and Methods

Plant Materials and Mutant DNA Preparation

Seeds of Triticale line wild-type Coorong (Coorong carries Sr27) were treated with ethyl methanesulfonate (EMS) following the protocol described by Mago et al. ((2015) *Nature Plants* 1, 15186). A kill-curve on 20-grains was initially produced with different concentrations, 0.1 0.2, 0.3, 0.4, 0.5 and 0.6% (v/v) to identify the dosage required to achieve 50% mortality. A total of 1960 seeds were treated with 0.3% EthylMethaneSulfonate for 12 hrs then washed thoroughly with water and sown in large pots (40 seeds per 30 cm pot) in a glasshouse with daylight and 23° C. day and 15° C. night temperature. Single heads from each M1 plant were threshed separately and M2 families from each plant were sown in a tray (30 M2 families per tray). Each tray also included resistant (Coorong) and susceptible (Rongcoo, triticale) controls. M2 families obtained as a single spike progeny from each M1 plant were tested for stem rust responses by inoculation with *Puccinia graminis* f. sp. *tritici* (Pgt) isolate Pgt21-0. Individual plants from segregating progenies were grown and progeny tested. Homozygous susceptible mutant and resistant sib pairs were recovered from these progenies.

Genomic DNA was extracted from wild-type Coorong triticale and homozygous susceptible mutants following the protocol described by Yu et al. (2017). The quality and quantity of the extracted DNA was first checked with a NanoDrop spectrophotometer (Thermo Scientific, Wilmington, DE) and then on a 0.8% agarose gel.

Resistance Gene Enrichment and Sequencing (RenSeq)

The Target enrichment of NLRs was performed by Arbor Biosciences (Ann Arbor, USA) following the MYbaits protocol using an improved version of the previously published Triticeae bait library available at github.com/steuernb/MutantHunter. Library construction was done by following the TruSeq RNA protocol v2. All enriched libraries were sequenced on a HiSeq 2500 (Illumina, CA, USA) using 250 bp paired end reads and SBS chemistry.

MutantHunter

To identify Sr27 contigs from mutants, the MutantHunter pipeline method of Steuernagel et al. ((2015) Bioinformatics 31:1665-7) was followed. Primary read sequencing data from wild-type Coorong and mutants were first trimmed for quality using Trimmomatic v0.38 (Bolger et al. (2014) Bioinformatics 30:2114-20) with the parameters ILLUMINACLIP: novogene_indexed_adapters.fa: 2:30:10:8: TRUE, LEADING: 28, TRAILING: 28, MINLEN: 20. Data from wild-type Coorong was then de novo assembled using the CLCGW v11.0.1 as paired-end with a length fraction of 0.95 and a similarity fraction of 0.98 and the remaining parameters as default. Contigs shorter than 1 kb were omitted from the final assembly using a custom script. An annotation of NBS-LRR motifs was created using the program NLR-Parser (Steuernagel et al. (2015) Bioinformatics 31:1665-7). Trimmed data of each mutant and wild type was mapped to the de novo assembly using BWA v0.7.15 (Li and Durbin (2009) Bioinformatics 25:1754-1760). Samtools v1.7.0 (Li et al. (2009) Bioinformatics 25:2078-9) was used for processing of resulting SAM files to retain only reads mapping in a proper pair with parameter -f 2, then removing duplicates and generating pileup files using parameters -BQ0 and -aa. SNV calling and subsequent candidate identification was performed using the following scripts from the MuTrigo pipeline (available via https at: github.com/TC-Hewitt/MuTrigo). Contig regions with high levels of SNPs in the wild-type data indicating poor assembly or read alignment were detected using Noisefinder.pyc with default parameters and masked prior to downstream analysis. Potentially mutated nucleotide positions were recorded from pileup files using SNPlogger.pyc with parameter -d 20. SNPtracker.pyc was used to retrieve contigs containing polymorphisms in two or more mutants using default parameters plus parameter -s C\>T G\>A indel. This translates to considering only polymorphisms with a minimum of 80% mutant allele frequency and selecting only for insertions, deletions, or C-to-T or G-to-A SNVs that do not share an identical position with another mutant or wild-type. Candidate gene contigs were aligned to the chromosome scale reference assembly of *Secale cereale* inbred line 'Lo7' (Rabanus-Wallace et al. (2019) bioRxiv: 2019.12.11.869693) and the *Triticum aestivum* cv. Chinese Spring reference (CSv1) assembly IWGSC RefSeq v1.0 (Appels et al. (2018) *Science* 361 (6403): eaar7191) using BLAST v2.7.1 (Altschul et al. (1990) *J. Mol. Biol.* 215:403-10). A de novo RNA transcript assembly was generated from Illumina RNAseq data from Coorong seedlings infected with Pgt (Upadhyaya et al. (2015) *Front Plant Sci.* 5:759) (downloaded from NCBI-SRA SAMN07836894, PRJNA415866) using CLCGW v11.0.1 (similarity fraction of 0.98 and the remaining parameters set as default).

Sr27 Gene Structure Confirmation

Primers were designed based on the genomic sequence of the two non-overlapping contigs no. 2413 and no. 5723 (Table 2). Primer pair Sr27c5723ExtF1 and Sr27c2413ExtR1 was used to amplify the non-overlapping region between the contigs no. 5723 and no. 2413 from genomic DNA of wild-type Coorong. Primer pair Sr27F and Sr27R1 was used for amplification for the full-length gene from genomic DNA of the wild-type and mutants for subsequent sequence comparison. All PCRs were performed using Phusion high fidelity DNA polymerase (NEB, USA) according to the manufacturer's instructions. Full-length Sr27 genomic sequence is shown in SEQ ID NO: 1. All mutants used in the RenSeq pipeline were re-confirmed by Sanger sequencing. Predicted exon-intron structures were confirmed by full cDNA amplification from RNA of triticale cv. Coorong. Total RNA was extracted using the PureLink™ RNA Mini Kit (Invitrogen catalog No 12183025, Thermo Fisher Scientific, MA USA) as per the manufacturer's instructions. cDNA synthesis was performed using the protocol described by manufacture (SMART™ PCR cDNA Synthesis kit, Cat No. 634902, Takara Bio USA Inc., (previously Clontech Laboratories Inc.).

Pgt Virulent Mutant Selection

Seedlings of the triticale cultivar Coorong at the 2-3 leaf stage (20 pots [15 cm] with 6-8 plants per pot) were inoculated with –100 g of stem rust isolate Pgt21-0 (Upadhyaya et al. (2015) *Front Plant Sci.* 5:759) using talc as a carrier (1:4; rust: Talc). Inoculated plants were incubated in a humid chamber maintained at 23° C. for 48 hrs. After this time plants were moved to a glasshouse maintained at 23° C./18° C. (day/night) under natural daylight. Plants were screened twice at 14 and 20 days post inoculation for any susceptible infection sites showing large pustule development typical of a susceptible interaction (infection type 3,4). More than 10 mutant pustules were detected and three of these were collected and re-inoculated onto the susceptible wheat line Morocco for amplification in isolation. After amplification the virulence of each mutant on Sr27 was confirmed by reinfection of wild-type Coorong plants. One mutant was further tested on the full Australian differential set for Pgt comprising a variety of wheat and triticale lines with different known resistance genes (Park (2007) *Aust. J.*

*Agric. Res.* 58:558-566) and showed an identical virulence profile to Pgt21-0 except for a single additional virulence for Sr27.

Identification of AvrSr27 Gene by Whole Genome Sequence Analysis

DNA was extracted from urediniospores of mutant Pgt lines with a CTAB method (Rogers et al. (1989) *Can. J. Bot.* 67:1235-1243) with some modifications as described (Upadhyaya et al. (2015) *Front Plant Sci.* 5:759), quality assessed with a Nanodrop Spectrophotometer (Thermo Scientific, Wilmington, DE) and quantitated using a broad-range assay in Qubit 3.0 Fluorometer (Invitrogen, Carlsbad, CA, USA). DNA library preparation and Illumina sequencing were performed by the Australian Genome Research Facility (AGRF) on HiSeq2500 with (250 bp PE reads, mutants M1 and M2) or MiSeq (300 bp PE reads, mutant M3) platforms and about 20 million reads obtained for each. Sequence reads were imported to CLC Genomics Workbench (CLCGW) version 10.0.1 or later (QIAGEN), filtered and trimmed to remove low quality ends, sequencing adapters and low-quality reads (Trim using quality score 0.01, maximum number of ambiguities allowed is 2). Reads were mapped to the karyon-phased chromosome level assembled Pgt21-0 reference annotated with 37036 gene models (Li et al. (2019) *Nature Commun.* 10, 5068) using high stringency settings (similarity fraction 0.98 and length fraction 0.95). Variant calling of each sample against the reference was performed using the "Basic Variant Detection" program with parameters: ignore non-specific matches; minimum coverage 10; significance 1.0%; minimum variant count 2; include broken pairs. The program "Compare variants within group" in CLCGW was used to identify variants specific to each sample as well as shared variants. Non-synonymous variants in secreted protein genes were predicted using the CLCGW tool "Amino Acid Changes" and curated manually by visual inspection of read mapping tracks in CLCGW. Read coverage statistics (mean read depth and percent coverage) for annotated genes were extracted using the "Create Statistics for Target Regions" program.

Example 2: Identifying the AvrSr27 Effector Recognised by Sr27

Figure 3:
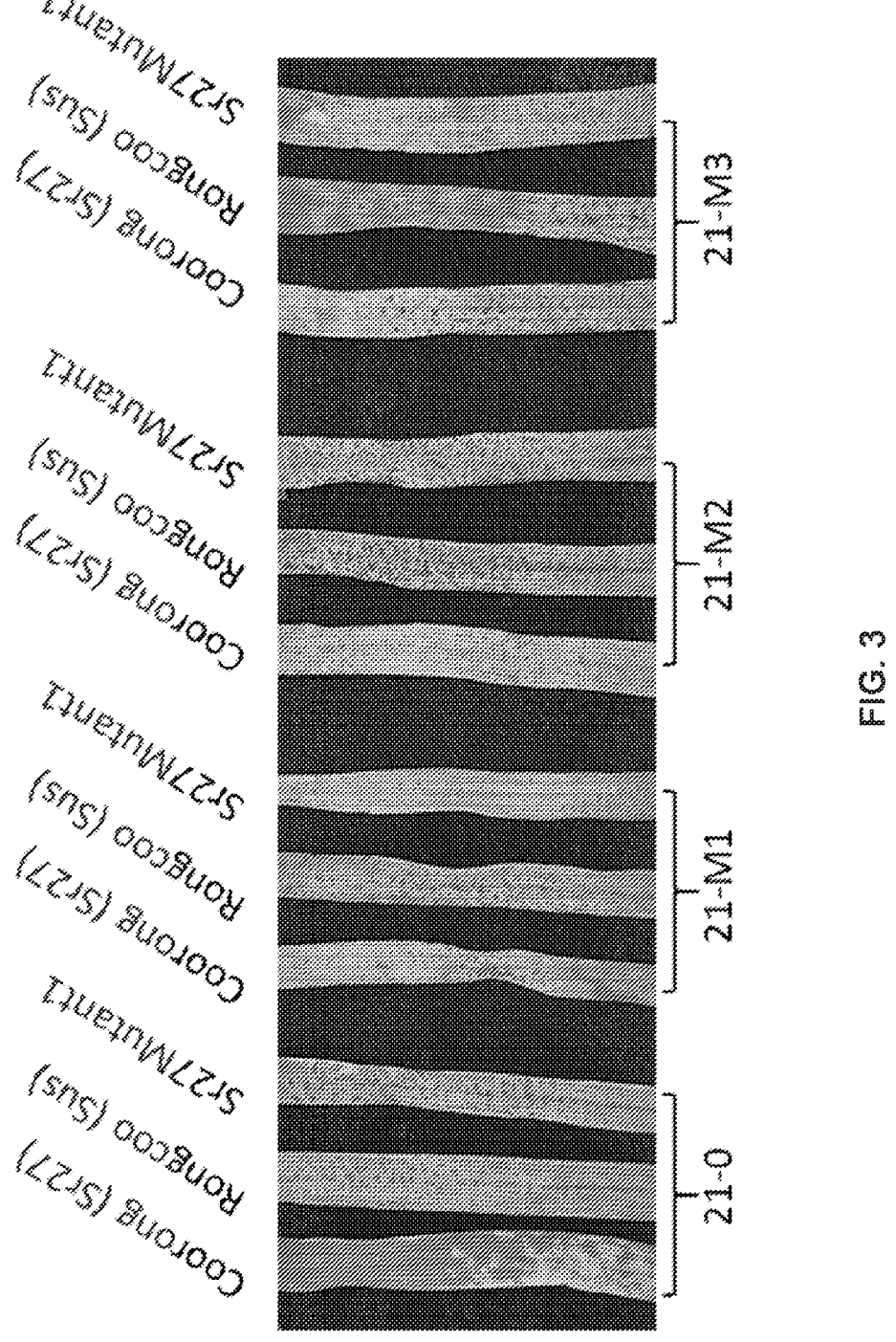
FIG. 3 is a photographic illustration of infection phenotypes of Pgt21-0 and three spontaneous mutants (21-M1, 21-M2 and 21-M3) on Triticale lines Coorong (contains Sr27), Rongcoo (rust susceptible) and a mutant line derived from Coorong with a loss of the Sr27 resistance gene (Sr27Mutant1). Image was taken 14 days after inoculation of seedling leaves.
Figure 4:
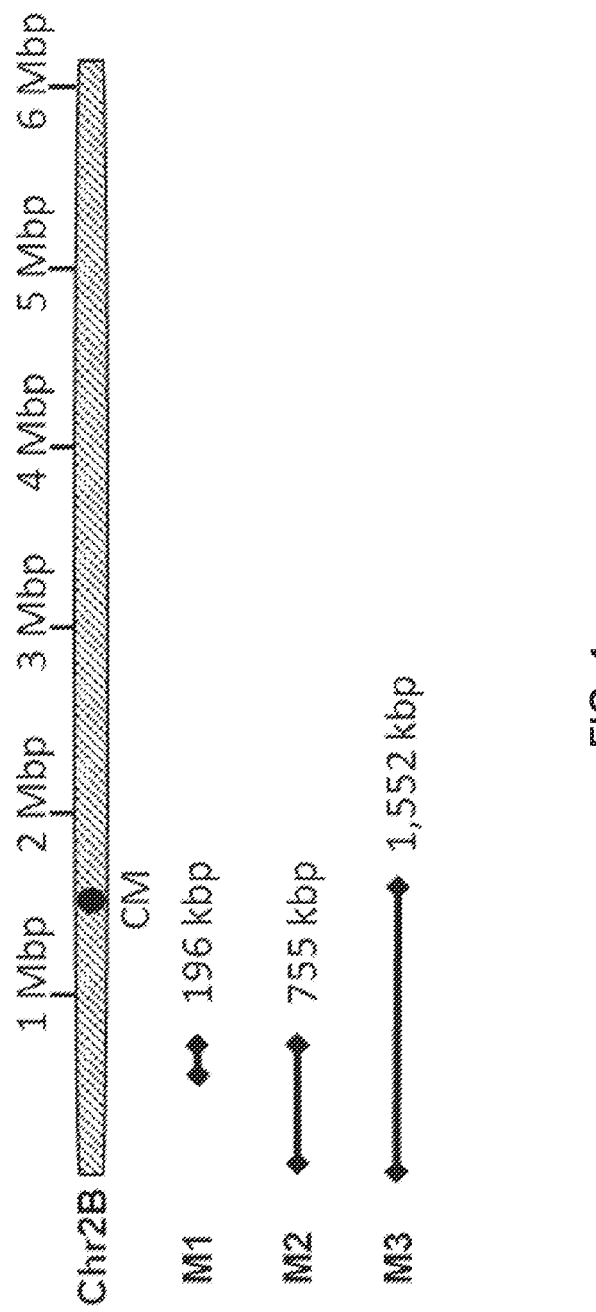
FIG. 4 is a schematic diagram of the positions and sizes (in kbp) of deletions in three Sr27-virulent mutants of Pgt21-0 (M1, M2 and M3) relative to chromosome 2B (hatched bar). The positions on the chromosome are indicated in 1 Mbp intervals from the 5' end with the centromere (CM) position indicated. The deletions were detected by read mapping of Illumina DNA sequence reads from Pgt21-0 and the three mutants onto the Pgt21-0 genome sequence.
Figure 5A:
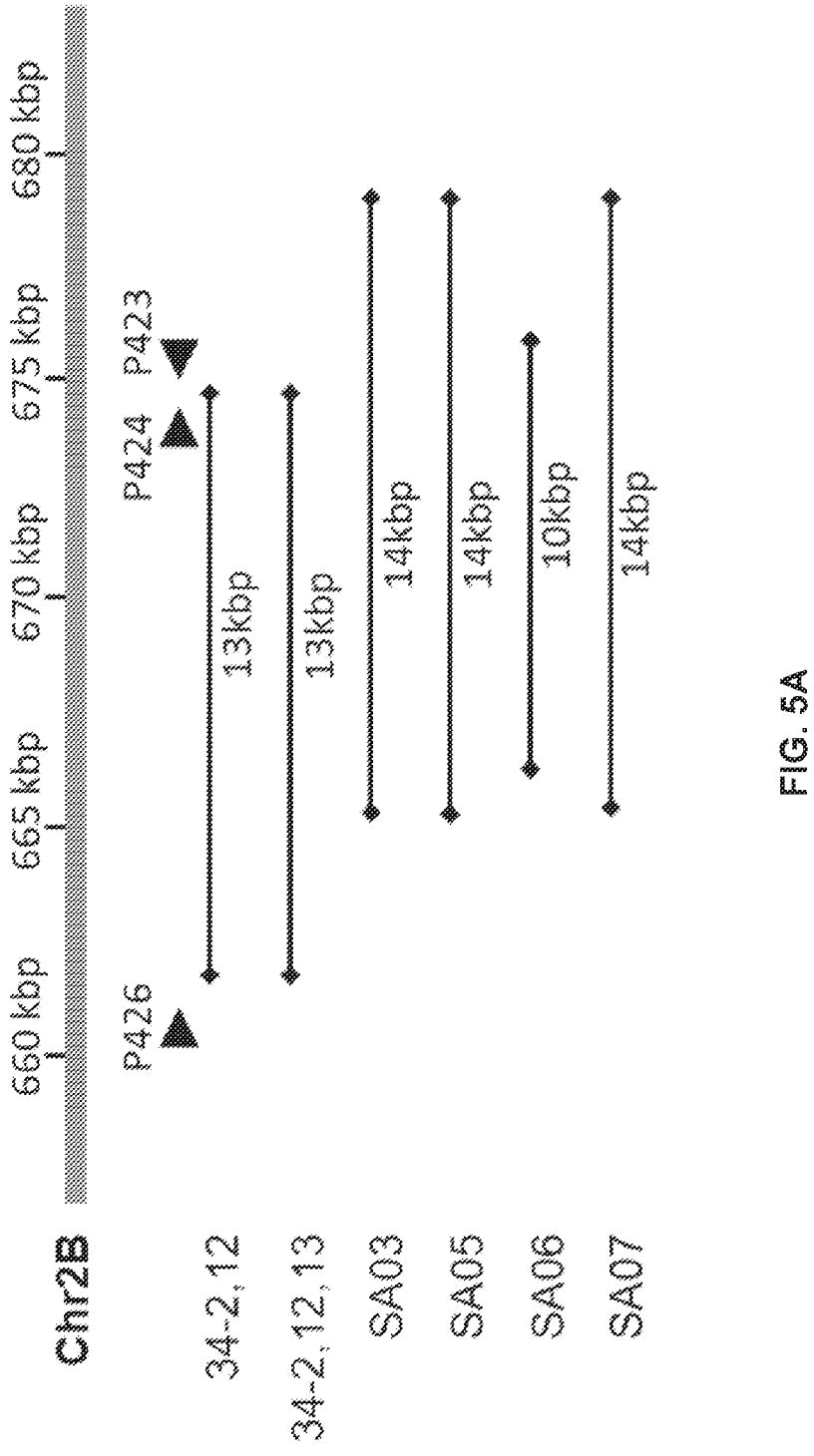
FIGS. 5A and 5B. Field isolates of Pgt with virulence for Sr27 contain small deletions on chromosome 2B.
Figure 5B:
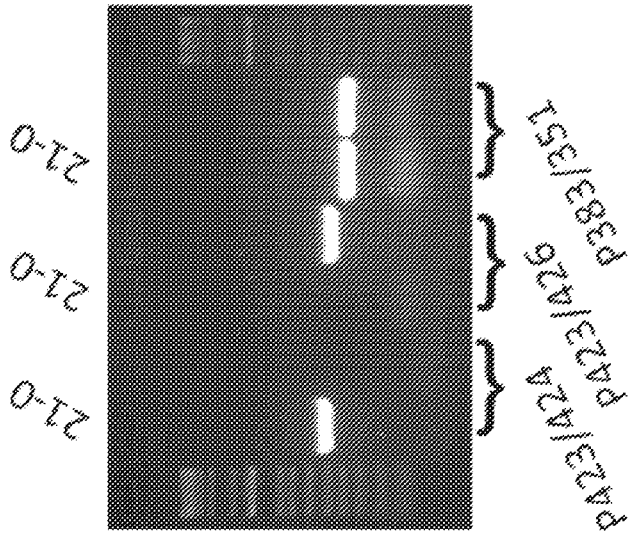

To identify spontaneous mutants of Pgt with a gain of virulence on Sr27, the inventors inoculated the avirulent isolate Pgt21-0 onto seedlings of the triticale cultivar 'Coorong' carrying Sr27. Three large single pustules were selected, purified in isolation and reinoculated onto Coorong to confirm their virulent phenotype (FIG. 3). The inventors extracted genomic DNA from each mutant and obtained Illumina sequence data. Illumina reads were mapped to the Pgt21-0 haplotype-resolved genome assembly (Li et al. (2019) *Nature Commun.* 10, 5068) to identify potential mutations. The first screen to identify SNPs causing amino-acid changes in secreted protein genes did not find any genes with such mutations in more than one Pgt21-0 mutant line. Next, the inventors looked for loss of read coverage as an indicator of potential deletion mutations. Each of the Pgt21-0 mutant lines showed a large number of genes with zero read coverage, all located on one end of chromosome 2B. Visualisation of read mapping to chromosome 2B revealed the three mutants each contained independent and overlapping deletions covering a portion of chromosome 2B, of which the smallest was 196 kilobase pairs (kbp) in size (FIG. 4). This region contains 50 annotated genes, of which five are predicted to encode secreted proteins. Previously two Australian Pgt isolates (34-2,12 and 34-2,12,13) that belong to a clonal lineage derived from Pgt21-0 and which had evolved virulence for Sr27 in the field were sequenced (Upadhyaya et al. (2015) *Front Plant Sci.* 5:759; Zhang et al. (2017). *Phytopath.*107:1032-1038). Analysis of read coverage revealed that these two isolates each contained a small deletion of 13 kbp (FIG. 5A) that spanned two of the secreted protein genes in this region (PGT21_006532 and PGT21_006593) along with a single adjacent gene on the distal side. No other genes in this region contained any changes in these two isolates. The inventors confirmed the presence of this deletion in the genome by PCR amplification of the deletion boundaries in Pgt21-0 and 34-2,12 (FIG. 5B). Sequence data generated from seven South African isolates was also examined (Lewis et al 2018), that are part of the same clonal lineage as Pgt21-0 (Li et al. (2019) *Nature Commun.* 10, 5068; Visser et al. (2019) *Phytopath.* 109:133-144) but have evolved independently in South Africa. Four of these isolates are virulent on Sr27 (Visser et al. (2009) *Mol. Plant Path.* 10:213-222) and must have evolved this phenotype independently of the Australian isolates. Three of these virulent isolates (SA03, SA05 and SA07) contain an identical ~14 kbp deletion that overlaps with the deletion in 34-2,12 and spans the two candidate secreted protein genes plus an additional gene on the proximal side, while the fourth isolate (SA06) contains an independent deletion of 10 kbp that spans just the two secreted protein genes (FIG. 5A). The remaining three avirulent isolates (SA01, SA02, SA04) from South Africa contain a similar sequence to Pgt21-0 in this region, as do three other Australian isolates (PGT098, PGT194, PGT326) of this lineage that are also avirulent on Sr27. A phylogenetic analysis of this clonally derived group of isolates places each of these deletion events in a separate branch of the lineage, consistent with the occurrence of three independent mutations to virulence on Sr27 during the diversification of this lineage (data not shown). The deletion of these two secreted protein gene candidates in three independent field-derived virulent isolates provides strong evidence that at least one of these genes confers the avirulence phenotype. These two genes are closely related to each other and encode predicted secreted proteins of 144 amino acids designated AvrSr27-1 (SEQ ID NO: 6) and AvrSr27-2 (SEQ ID NO: 8) (FIG. 6).

Example 3: Transient Expression Validation of Sr27 Function

Figure 7:
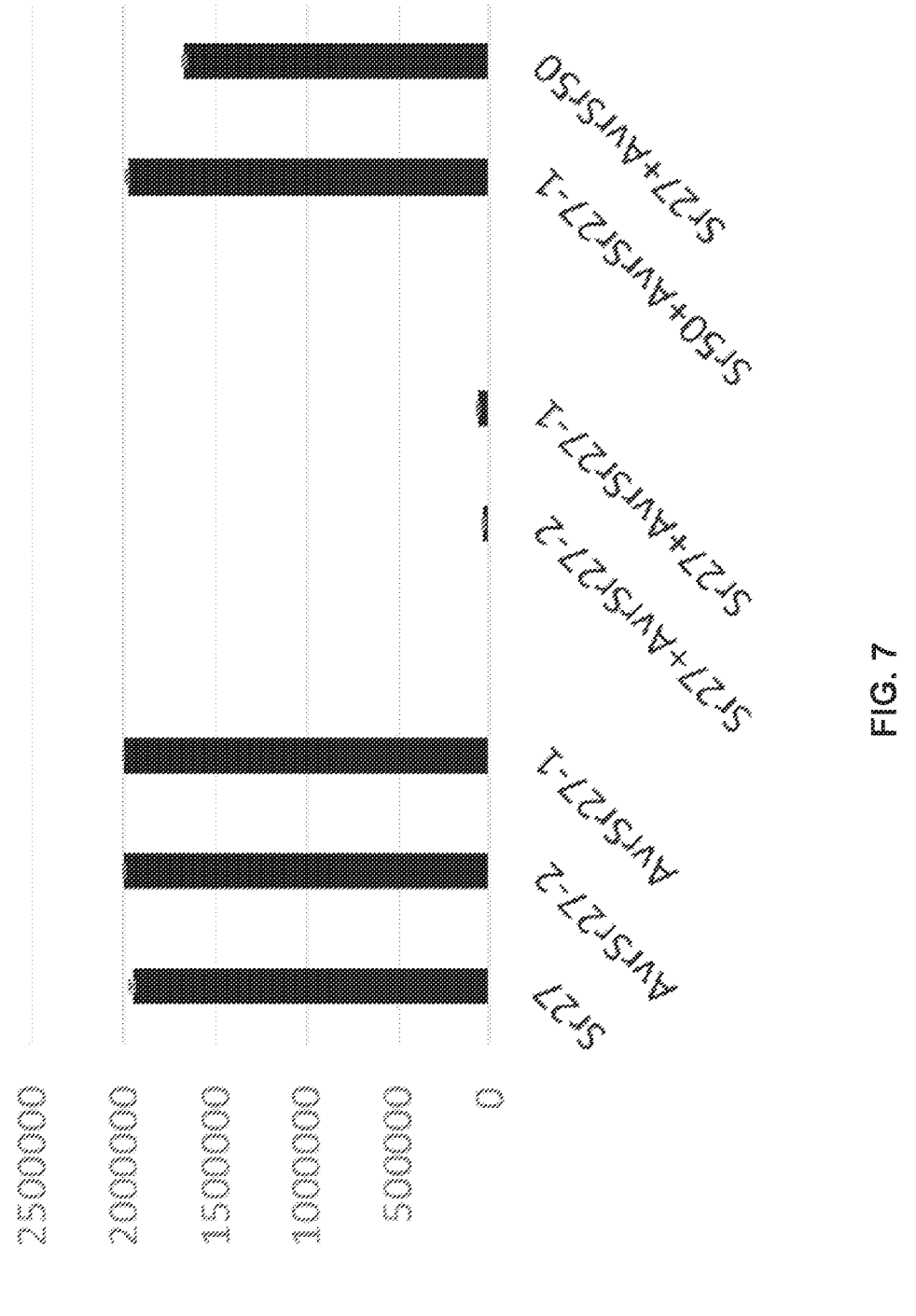
FIG. 7 is a graphical representation that shows confirmation of Sr27 resistance function. Luciferase activity (luminescence units y-axis) was detected in protoplasts co-expressing Sr27 or AvrSr27-1 or AvrSr27-2 alone, Sr27 and AvrSr27 variants in combination, Sr50 plus AvrSr27-1 or Sr27 plus AvrSr50.

To confirm the function of the Sr27 candidate gene, we used a wheat protoplast transfection assay as described below to co-express the gene with the AvrSr27 variants identified above as well as the reporter gene luciferase. Recognition between the resistance and avirulence gene in this assay leads to cell death and therefore a reduction in the expression of the co-transformed luciferase reporter gene which is detected by its bioluminescence (Saur et al. (2019) *Plant Methods* 15, 118). Co-expression of the Sr27 candidate gene with each of the AvrSr27 gene variants led to a strong reduction in luciferase activity compared to the expression of Sr27 or AvrSr27 genes in the protoplast alone (FIG. 7). This was a specific recognition response as no loss of reporter gene expression was seen when Sr27 was co-expressed with the unrelated Pgt avirulence gene AvrSr50 (Chen et al. (2017) *Science* 358:1607-1610), nor when AvrSr27-1 was co-expressed with the unrelated wheat resistance gene Sr50 (Mago et al. (2015) *Nature Plants* 1, 15186). This confirms that the cloned Sr27 sequence confers specific recognition to the AvrSr27 effector from Pgt and hence is responsible for resistance to Pgt isolates expressing the AvrSr27 gene.

Thus, the inventors demonstrated that the Sr27 coding region, when expressed in wheat protoplasts under the control of an operably linked ubiquitin promoter, is sufficient to confer recognition of the corresponding effector AvrSr27 from the wheat stem rust fungus (Pgt). The effector was identified by mutation analysis, which located it within 196 kbp deletion on chromosome 2B of Pgt21-0. Subsequent analysis found two genes that were independently deleted in three different Pgt that acquired virulence on Sr27. The availability of the cloned effector recognised by Sr27 facilitates genetic screening of wheat stem rust isolates for the presence of this effector and therefore their predicted virulence on Sr27.

Materials and Methods

Construct Generation

AvrSr27 gene sequences (shown in SEQ ID NOS: 5, 7, and 9) with the predicted signal peptide excluded and replaced by a single methionine start codon were amplified from cDNA from purified haustoria of Pgt21-0 using Phusion high-fidelity DNA polymerase (Thermo Scientific, Wilmington, DE) and cloned into pENTR™/D-TOPO® according to manufacturer's (Invitrogen™, Thermo Fisher Scientific, MA, USA) instructions. Full-length Sr27 cDNA was also cloned into pENTR™/D-TOPO®. For wheat protoplast transfection Sr27 and AvrSr27 sequences were inserted into the p35s-pUbi-GTW-GFP (Akamatsu et al. (2013) *Cell Host Microbe* 13:465-476) using Gateway® Technology (Life Techonologies™). Primers used for PCR are shown in Table 2. All plasmids were confirmed by sequencing and analysed using Vector NTI Advance (Life Technologies, Thermo Fisher Scientific, MA, USA) or CodonCode Aligner V.4.0.4 (CodonCode Corporation, MA, USA) software. Plasmids encoding GFP (Arndell et al. (2019) *BMC Biotechnol.* 19:71) and Luciferase (Saur et al. (2019) *Plant Methods* 15, 118) were previously described.

Protoplast Expression Assay

Wheat seedlings were grown in a growth chamber under shade at 25° C. degrees with a photoperiod of 16 h of light for 7-9 days. Wheat protoplast isolation and transformation were performed as described (Arndell et al. (2019) *BMC Biotechnol.* 19:71). High quality plasmid DNA was isolated by using Qiagen Endo-free Plasmid Maxi kits (Cat. No. 12362). DNA concentrations were adjusted to 1 μg/μl and 10 μg of each plasmid was used in co-transformation experiments. After a 24-hour incubation in the dark at 23° C., the luciferase activity assay was performed as described by Saur et al. ((2019) *Plant Methods* 15, 118) using the Luciferase Assay System (Promega, catalog no. E1501) following the manufacturer's instructions.

Example 4: Comparison of Sr27 to Other Resistance Genes

Figure 8:
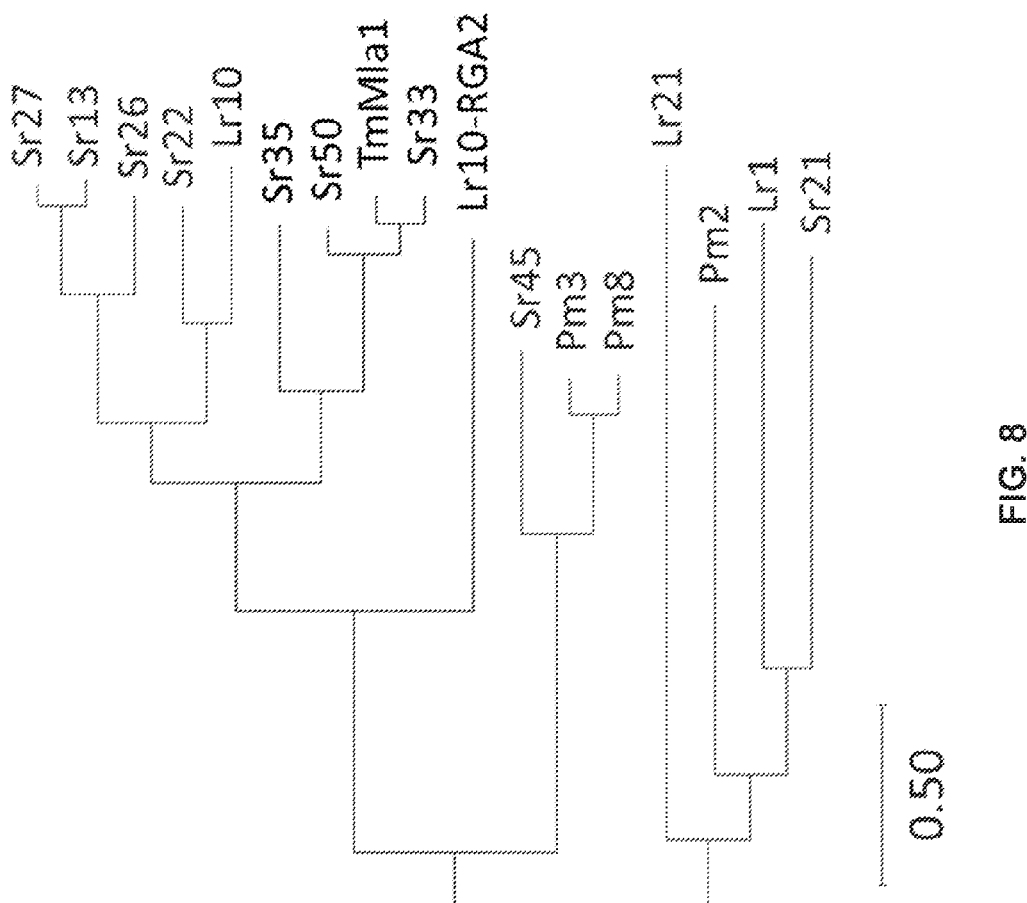
FIG. 8 is a maximum likelihood phylogenetic tree comparing the Sr27 amino acid sequence to protein sequences of known wheat resistance proteins. Scale shows amino acid sequence divergence.

According to BLAST best hits against IWGSC CS ref v1.0, the location of the closest homologs of the Sr27 candidate in Chinese Spring reference v1.0 was on chromosome 6B (see Example 1). The inventors further extended the list of homologous sequences by performing BLAST against the non-redundant protein data base at NCBI (results not shown). The top hit was an unnamed protein product from *Triticum turgidum* subsp. durum (GenBank Accession VAI63620.1) and had 90.5% amino acid identity to the Sr27 protein. To determine the evolutionary distance and degree of diversity between Sr27 and other cloned CNL type R genes from wheat at the protein sequence level, the inventors aligned the Sr27 protein to 16 CNL type R genes identified from wheat and performed a phylogenetic analysis as described below (FIG. 8). The closest R gene to Sr27 from the selected group is the wheat stem rust resistance gene Sr13 with 86.7% amino acid identity.

Methods

Phylogenetic Analyses

Phylogenetic and molecular evolutionary analyses were conducted using MEGA version X (Kumar et al. (2018) *Mol. Biol. Evol.* 35:1547-1549). Protein sequences of Sr27 and other wheat resistance proteins were aligned by CLUSTAL and a Maximum likelihood tree constructed.

Example 5: Confirmation of Sr27 Function in Transgenic Plants

The Sr27 gene construct driven by the ubiquitin promoter (described in Example 3) was transferred into the wheat cultivar Fielder by *Agrobacterium*-mediated transformation and transgenic lines generated as described below.

*Agrobacterium*-mediated transformation of wheat was performed as described (Ishida et al. (2015) "Wheat (*Triticum aestivum* L.) transformation using immature embryos", In: Wang K (ed), *Agrobacterium* Protocols, vol. 1, 3rd, Springer, New York, pp. 189-198). Wheat plants of the cultivar Fielder were propagated under glasshouse growth conditions using a 24° C., 16 h light/18° C., 8 h dark growth regime and plants were fertilised fortnightly with Aquasol (Yates, Clayton, Australia). Wheat heads were tagged at anthesis and harvested 12-14 days post anthesis for transformation experiments as described by Ishida et al. (Id.) and as adapted at CSIRO, Canberra, Australia (Richardson et al. (2014) *Plant Cell Tiss. Org.* 119:647-659). Briefly seeds were surface sterilised for 10 min in a 0.8% sodium hypochlorite solution. Embryos were removed from the seed under aseptic conditions and co-cultivated with *Agrobacterium* strains containing the Sr22 and Sr45 genomic fragment binary construct for 2 days on WLS-AS medium (Ishida et al. 2015) in the dark. After co-cultivation embryonic axes were excised with a scalpel and explants then transferred to WLS-Res medium and placed in the dark at 24° C. After 5 days explants were transferred to WLS-H15 callus induction media containing 15 mg/ml of hygromycin (Hyg) for callus formation. Two weeks later, the resulting calli were bisected and placed on WLS-H30 (30 mg/l of Hyg) for 3 weeks in the dark. Callus was then regenerated on LSZ-H15 (15 mg/l Hyg) medium in 200 μmols m$^{-2}$ s$^{-1}$ light at 24° C. Shoots were transferred to LSF-H15 (15 mg/l Hyg) medium to allow root formation and once robust root systems developed, plants were transferred to soil and maintained in the glasshouse.

Figure 9:
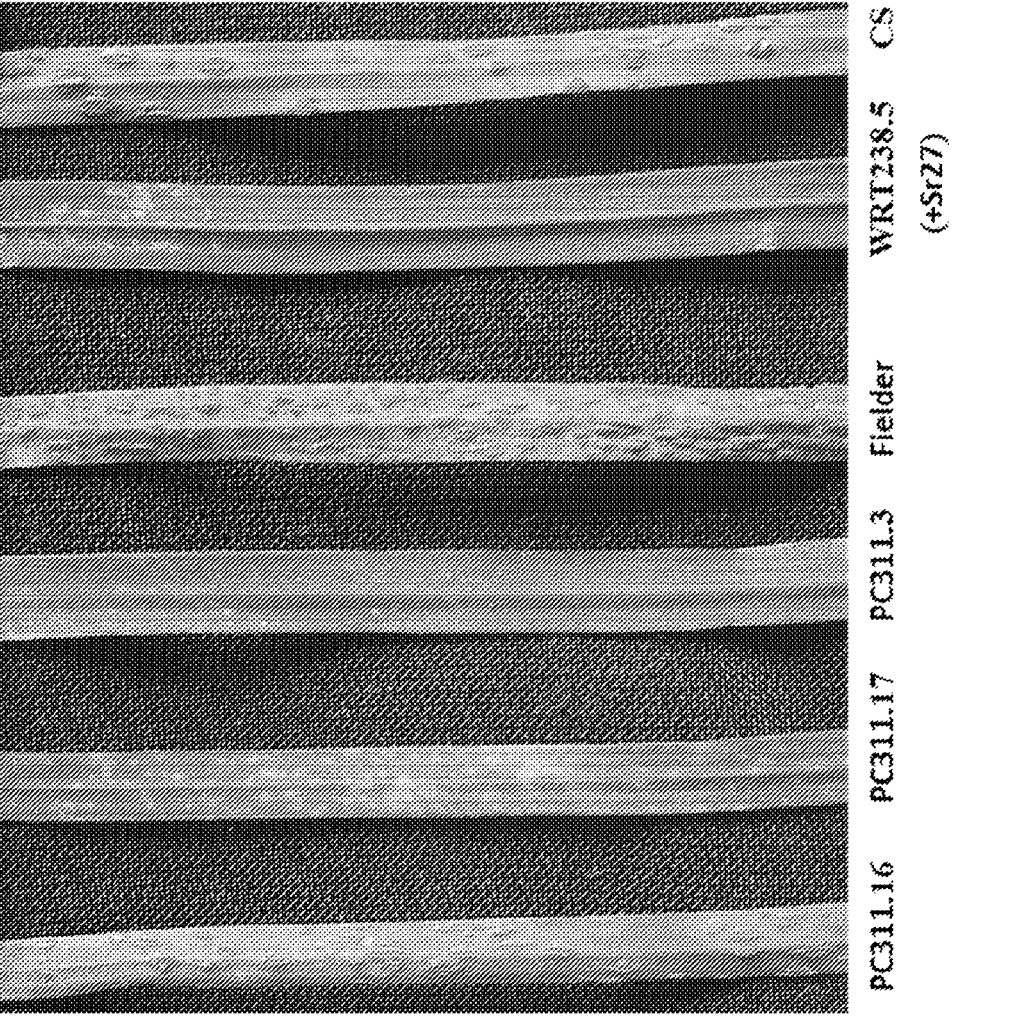
FIG. 9 shows the phenotypes of exemplar T1 families containing the Sr27 transgene and control plants infected with stem rust race 98-1,2,3,5,6, and scored 10 days post infection. The image shows a representative T1 plant from two transgenic lines (PC311.3 and PC311.17) containing the Sr27 transgene, a non-transgenic line recovered from tissue culture (PC311.16), the susceptible parent Fielder, Chinese Spring WRT258.5 containing the native Sr27 gene and the susceptible parent Chinese Spring (CS).

T0 lines were screened by PCR with primers for the transgene (Sr27c5723 F×Sr27c5723 R, Table 2) and three positive lines were identified (PC311.3, PC311.17 and PC311.18). T1 seed was harvested from the three positive lines as well as a fourth line lacking the Sr27 transgene (PC311.16). Eleven or twelve progeny of each line were grown in a growth cabinet (23° C., 16 h light) along with control lines (see Table 1). Two-week-old seedlings were inoculated with Pgt race 98-1,2,(3),(5),6 to which Sr27 confers resistance. Rust reactions were assessed after 10-15 days (Table 1). For PC311.3 and PC311.17, all T1 progeny showed strong resistance to Pgt with infection types characterised by tiny necrotic infection spots with no pustule formation, similar to the phenotype observed in wheat line WRT258.5 carrying Sr27 (FIG. 9). T1 progeny of the third Sr27 transgenic line, PC311.18, segregated for resistance with 10 resistant and 1 susceptible progeny (Table 1). PCR analysis confirmed that the single PC311.18 T1 progeny susceptible plant did not contain the Sr27 transgene while the resistant T1 progeny contained Sr27. In contrast the susceptible lines Chinese Spring and Fielder showed high infection types with large uredia and no chlorosis or necrosis (see FIG. 9), as did the PC311.16 line recovered from transformation that did not contain the Sr27 transgene (FIG. 9). These data confirm that the Sr27 transgene confers stem rust resistance in transgenic wheat when expressed by the ubiquitin promoter. T1 progeny of each of the three positive lines were further tested by inoculation with leaf rust (*P. triticina*) isolate 76-1,3,7,9,10,12,13 and stripe rust (*P. strii-formis*) isolate 198 E16 A+ J+ T+ 17+. All progeny were fully susceptible to the leaf rust and stripe rust isolates confirming that the Sr27 transgene conferred specific resistance to stem rust and this resistance was not due to non-specific activation of defense responses effective against rust pathogens.

TABLE 1

Results of Stripe Rust Resistance Assays
of Sr27 Transgenic Wheat Lines

| Family | Transgene PCR | No. of progeny infected with Pgt 98-1, 2, 3, 5, 6 | No. of resistant seedlings | No. of susceptible seedlings |
|---|---|---|---|---|
| PC311-3 | + | 11 | 11 | 0 |
| PC311-16 | – | 11 | 0 | 11 |
| PC311-17 | + | 12 | 12 | 0 |
| PC311-18 | + | 11 | 10 | 1 |
| Fielder (susc) | – | 11 | 0 | 11 |
| WRT 258.5 (Sr27+) | – | 15 | 15 | 0 |
| Chinese Spring (susc) | – | 16 | 0 | 16 |

Example 6: Sequences of Primers Used in Cloning of Sr27

In Table 2 below, the nucleotide sequences of primers used in the cloning of Sr27 from triticale cv. Coorong as described in the Examples above are provided. The nucleotide sequences of these primers are offered by way of illustration example for purposes of clarity of understanding and not by way of limitation.

TABLE 2

Primer Sequences

| Primer Name | SEQ ID NO | Sequence | Target |
|---|---|---|---|
| Sr27F | 9 | CCTGTTCGATCACTGGTCG | Sr27 forward |
| Sr27F2 | 10 | GTGAAGATGGTCTGCATTGTTGGATCG | Sr27 |
| Sr27R1 | 11 | GATGGTATATACCGTGGTCCGACAAAT | Sr27 reverse |
| Sr27R2 | 12 | CGGAGGTTAAGCGGCGGAGA | Sr27 |
| Sr27R3 | 13 | GGTTTTGTGTGCATAGTTTACCAAGAG | Sr27 |
| Sr27c5723F | 14 | ATGAACCCAAGGCTGAGTTG | Sr27 |
| Sr27c5723R | 15 | ACATGCAAATAAGGGCTTCC | Sr27 |
| Sr27c2413F | 16 | GTAAGGCTCCAAGGATGCAG | Sr27 |
| Sr27c2413R | 17 | TAAGTTTCCCGACGGAATTG | Sr27 |
| Sr27c5723ExtF1 | 18 | AAGAACAAGTGAAGATGGTCTGC | Sr27 3' end contig 5723 |
| Sr27c2413ExtR1 | 19 | TTCTGTAGAATAGTTGTCTTGAGTGCTC | Sr27 5' end contig 2413 |
| Sr27c2413ExtF1 | 20 | TACGAGGAAGCGAAAAACAGC | Sr27 |
| Sr27cSeq1R | 21 | ATCTTCTCAGTGAAGCCATC | Sr27 |
| Sr27cSeq2R | 22 | AAATGTGACTTGATACATCTG | Sr27 |
| Sr27cSeq3F | 23 | ATAGTGATTGACGACATATGG | Sr27 |
| Sr27cSeq4F | 24 | GATTCATTCGACAAGAAGGT | Sr27 |
| P341 | 25 | ATTCAGATTTAAGAGTCTTGATTGAGTCCCCATG | PGT21_006334 reverse |

TABLE 2-continued

Primer Sequences

| Primer Name | SEQ ID NO | Sequence | Target |
|---|---|---|---|
| P373 | 26 | CACCATGCAATTAGCCAGTGTCTTATGTG | PGT21_006334 forward |
| P351 | 27 | GTCTTCCTACCTGTGTTGGCGCCTTGCAAAATG | AvrSr50 reverse primer |
| P383 | 28 | CACCATGATGCATTCAATTATCTTTCAAACACTCC | AvrSr50 forward primer |
| P414 | 29 | TTACCATCTTCTGTGACACTCTGGG | AvrSr27-2 reverse |
| P415 | 30 | TTACCATCTGCTGTGACACTCTGG | AvrSr27-1 reverse |
| P416 | 31 | CACCATGGCAATGACACCACATCACCAAAGCAAT | AvrSr27-1/-2 27 aa signal peptide clipped CDS 5' with CACCATG for directional Topo cloning |
| P418 | 32 | CCATCTTCTGTGACACTCTGGGCTTG | AvrSr27-2 CDS 3' without stop codon |
| P419 | 33 | CCATCTGCTGTGACACTCTGGGCTTG | AvrSr27-1 CDS 3' without stop codon |
| P420 | 34 | CACCATGCATTACATCACCCCCATAATCCTT | AvrSr27-1/-2 forward |
| P421 | 35 | CACCATGGCAGGAAGTCTTGTGGGTGCAATGAC | AvrSr27-2 21 aa signal peptide clipped CDS 5' with CACCATG for directional Topo cloning |
| P422 | 36 | CACCATGGCAGGAGGTCTTGTGGGTGCAATGAC | AvrSr27-1 21 aa signal peptide clipped CDS 5' with CACCATG for directional Topo cloning |
| P423 | 37 | AAGTGGATAACGTACTCTGCACAAC | upstream of 5' deletion boundary in 34-2, 12 |
| P424 | 38 | AGTGACTGCAATTCACCAATATTTCG | Internal to deletion region in 34-2, 12 |
| P426 | 39 | AACATTCAGTGCGAGGAATGGGGAG | downstream of 3' boundary region in 34-2, 12 |

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A transgenic wheat plant or transgenic wheat seed comprising stably incorporated in its genome a heterologous polynucleotide construct comprising a nucleotide sequence selected from the group consisting of:
   (a) the nucleotide sequence set forth in SEQ ID NO: 1, 2, or 4;
   (b) a nucleotide sequence encoding the amino acid sequence set forth in SEQ ID NO: 3; and
   (c) a nucleotide sequence encoding an amino acid sequence having at least 95% sequence identity to the amino acid sequence set forth in SEQ ID NO: 3, wherein the heterologous polynucleotide construct is capable of conferring resistance to stem rust to a wheat plant comprising the heterologous polynucleotide construct.

2. The transgenic wheat plant or transgenic wheat seed of claim 1, wherein the nucleic acid molecule of (c) encodes a protein comprising a coiled-coil domain, a nucleotide-binding domain, and a leucine-rich repeat domain.

3. The transgenic wheat plant or transgenic wheat seed of claim 2, wherein at least one of the coiled-coil domain, the nucleotide-binding domain, and the leucine-rich repeat domain comprises an amino acid sequence having at least 95%, 96%, 97%, 98%, 99%, or 100% amino acid sequence identity to the corresponding domain in SEQ ID NO: 3.

4. The transgenic wheat plant or transgenic wheat seed of claim 1, wherein the polynucleotide construct further comprises a promoter operably linked to the nucleotide sequence for the expression of the nucleotide sequence in a plant.

5. The transgenic wheat plant or transgenic wheat seed of claim 4, wherein the promoter is selected from the group consisting of pathogen-inducible, constitutive, tissue-preferred, wound-inducible, and chemical-regulated promoters.

6. The transgenic wheat plant or transgenic wheat seed of claim 1, wherein the transgenic wheat plant or transgenic wheat seed comprises enhanced resistance to wheat stem rust caused by at least one race of *Puccinia graminis* f. sp. *tritici*, relative to a control wheat plant.

7. A method for enhancing the resistance of a wheat plant to wheat stem rust, the method comprising introducing a heterologous polynucleotide construct into at least one wheat plant cell, the heterologous polynucleotide construct comprising a nucleotide sequence selected from the group consisting of:

(a) the nucleotide sequence set forth in SEQ ID NO: 1, 2, or 4;

(b) a nucleotide sequence encoding the amino acid sequence set forth in SEQ ID NO: 3; and (c) a nucleotide sequence encoding an amino acid sequence having at least 95% sequence identity to the amino acid sequence set forth in SEQ ID NO: 3, wherein the heterologous polynucleotide construct is capable of conferring resistance to stem rust to a wheat plant comprising the heterologous polynucleotide construct.

8. A method of limiting wheat stem rust in agricultural crop production, the method comprising planting a transgenic wheat seed and growing a wheat plant under conditions favorable for the growth and development of the wheat plant, wherein the transgenic wheat seed comprises stably incorporated in its genome a heterologous polynucleotide construct comprising a nucleotide sequence selected from the group consisting of:

(a) the nucleotide sequence set forth in SEQ ID NO: 1, 2, or 4;

(b) a nucletoide sequence encoding the amino acide sequence set forth in SEQ ID NO: 3; and (c) a nucleotide sequence encoding an amino acid sequence having at least 95% sequence identity to the amino acid sequence set forth in SEQ ID NO: 3, wherein the heterologous polynucleotide construct is capable of conferring resistance to stem rust to a wheat plant comprising the heterologous polynucleotide construct.

9. A transgenic wheat plant identified by detecting in the wheat plant the presence of the R gene, Sr27, wherein the transgenic wheat plant comprises a heterologous polynucleotide construct comprising the R gene, and wherein the R gene comprises a nucleotide sequence selected from the group consisting of:

(a) the nucleotide sequence set forth in SEQ ID NO: 1, 2, or 4;

(b) a nucleotide sequence encoding the amino acid sequence set forth in SEQ ID NO: 3; and (c) a nucleotide sequence encoding an amino acid sequence having at least 95% sequence identity to the amino acid sequence set forth in SEQ ID NO: 3, wherein the R gene is capable of conferring resistance to stem rust to a wheat plant comprising the R gene;

or a transgenic seed of the transgenic wheat plant, wherein the transgenic seed comprises the heterologous polynucleotide construct.

\* \* \* \* \*

SEQUENCE LISTING

<160> NUMBER OF SEQ ID NOS: 39

<210> SEQ ID NO 1
<211> LENGTH: 3956
<212> TYPE: DNA
<213> ORGANISM: x Triticosecale

<400> SEQUENCE: 1
cctgttcgat cactggtcgt gcattcgagc ttttaggcca tggaggcggc tctggtgacc     60

```
gtggcgacgg gagtcctcaa acctgtcctg gggaagctgg ccaccctgct cggcgacgag    120
tacaagcgtt ttaagggtgt gcgcaaggag atcaggtctc tcactcatga actcgccgcc    180
atggaggctt ttctcctcaa gatgtcggag gaggaggagg atcccgatgt gcaggataaa    240
gtctggatga atgaggtgcg ggaattgtcc tatgacatgg aggacgccat cgacgacttc    300
atgcaaagca ttggtgacaa agacgaaaag ccggatggct tcactgagaa gatcaaggcc    360
actctaggca agttgggaaa tatgaaggct cgtcatcgaa ttggcaagga gatacatgat    420
ctgaagaaac agatcattga ggtgggcgac aggaatgcaa ggtacaaggg acgcgagatc    480
ttctccaagg ccgtcaatgc gaccgttgac cctagagctc ttgctatctt tgagcatgca    540
tcaaagctcg tcggaattga tgaacccaag gctgagttga tcaagttgtt aactgacgag    600
gatggagttg catcaacaca agaacaagtg aagatggtct gcattgttgg atcgggagga    660
atgggcaaaa caactcttgc aaaccaagtg tatcaagaga tgaaagagga attcaagttt    720
aaggctttca tatcagtgtc acgaaatcca gatatgatga atatcttgag aaccctcctc    780
agtgaaattg ggtgtcaaga ttatgctcac actgaagcag ggagcataca acaactaata    840
agcaagatta ccgattacct agcagaaaaa aggtactatt atatttcttt aaactcactt    900
ctcgcccata gaaagttaaa ttaagaattc tcacatagaa aaaacactcc taataaagaa    960
tcaaaataat tatataatta aattatatac tttttgggtg aaaattaatt gccaaatgta   1020
tggaagccct tatttgcatg tactttacta cttcctccgt tcctaaatat aagtctttgg   1080
agagatttca ctatggacca catacgaagc aaaatgagtg aatctacact ctaaaatgca   1140
tctatataca tccgtatgtg gttcatggtg aaatctctag aaagacttat atttaggaac   1200
ggagggagta gttaactagg ttgttgtatt tggagggaaa ataagtctta tataggtagg   1260
aacatttgat tagtaggtat tcggcatgta tgtgcatctc agaatgcata tagactaaaa   1320
gacaatcttt tccgcaataa agaaatatca tcaatcttca atcaagcaag tatgctactc   1380
cctccgtccc aaaattcttg tcttagattt gtctaaatac agatgtatca agtcacattt   1440
tagtattaga aacatccgta tctgggcaaa tctaagacaa gaattttggg acggagggag   1500
tacatgatat gtaccactct aagtgcttag agctcttttg ctcttatatg gcctatctag   1560
gaaaacatat tttgtttagt aagtgcttag agtagaaaca ctatataggt attttctagc   1620
catgtggccc tgtttaagtt gcatagtacc ctagagccga tccattatct tttgcatgtt   1680
gccaatgaga acatggaaat ttctctttct tcttattttg cttgtacgct tcgttttaac   1740
acatcatact aactattact actaaaaaat catgtgcagg tattttatag tgattgacga   1800
catatgggac gtcaaaacat gggacgttat taagtgcgca ttccccatga ccagatgcgg   1860
tggtgtaata atcaccacca ctcggctgag tgatgttgca tgttcgtgtc attcatcaat   1920
cggtggccat atttataata taaggcctct taatatggag cactcaagac aactattcta   1980
cagaagatta ttcagctccg aagaagattg cccttcatcg ctcgtgaaag tttcttatca   2040
aatcttggaa aaatgtgatg ggttgccttt ggcaatcatt gctatagctg gtttgttggc   2100
taacacagga agatcagagc atcaatggaa ccaagtgaaa gattcaattg gtcgtgcact   2160
tgaaaggaat cctagtgtcg aagtaatgat aaagatattg tcacttagtt actttgatct   2220
tcctccgcat ctaaaaacat gtctcttgta tctcagtata ttcccggaag attctattat   2280
tgagaagaaa acactaatat caagatggat tgctgaagga ttcattcgac aagaaggtag   2340
atatactgca tatgaggtag gagtgaggtg ttttaatgag ctcgtcaaca ggagtttgat   2400
```

-continued

```
ccaacctgtg aagaaagacg attataaggg gaagagttgt cgagttcacg atataattct    2460
tgatttcata gtatccaagt ccattgaaga gaactttgtt acttttgttg gtgtccccag    2520
tttaactacc gtgacacaag gcaaagtccg ccgtctctcc atgcaagttg aagagaaggt    2580
ggattctatt ttgccaatga gcctgatatt atctcatgtc cgatcactta acatgttcgg    2640
gaatacagtg agtattcctt cgatcatgga gttgaggcat ttgcgtgtcc ttgatttcgg    2700
aggaaacaga ctattggaaa accgtcatct cgcgtatgta gggatgctgt ttcagctaag    2760
gtacctcaac atttacatga cagcagtaag cgagctcccg gaacaaatcg gacacttaca    2820
gtgcttagag atgttggaca tcaggcatac atgggtgtct gagctgccag ccagtattgc    2880
caatctcggc aaactggcac acttacttct tagctcaaat actggcacaa atgttaagtt    2940
tcccgacgga attgctaaga tgcaatcact ggaggctttg catagcgtta acacctgcaa    3000
tcagtcatat aactttctgc aagggcttgg tcagctaaag aatctgagga agctgggcat    3060
taactatcgg ggtgttgccc acgaagacaa ggaagttatt gcttcttctc ttggtaaact    3120
atgcacacaa aacctttgtt ctctaactat gtggaatgat gacgacgact tcttgctaaa    3180
tacatggtgc acttctccgc cgcttaacct ccgaaaactt gtcatatggg gttgtatatt    3240
cccaaaggtt ccgcattggg taggatcact cgtcaaccta cagaagttac acttggaagt    3300
ggggagagga acccggcatg aagatatctg catccttgga gccttacccg ctctgttcac    3360
tctgggtcta cgaggaagcg aaaaacagcc ttcttgtgaa aatagaaggc tggcagttag    3420
tggtgaagct gggttccgat gcctgaggaa gtttaaatac tggaggtggg gggattggat    3480
ggatcttatg tttacggcaa aatgtatgcc caggctagaa aaactgaaga ttatatttta    3540
cggccatgcc gaagatgagg ctcccatcat tcctgctttc gatttcggga tcgaaaacct    3600
gtccagcctc actactttca aatgtcacct aggttatggg cctatggcaa cgaaaattgt    3660
tgacgctgta aaggcttctc tggacagagt agttagcgca catcccaacc accttactct    3720
aatcttcact tattgttgtg tgttttgtaa gagttatgac tgtggtggtc gatgccttct    3780
gtctagagat cttcagtcat cctccgaatc tacttgagta gagtcaagac catgcgtacg    3840
tgcttaattc ttctcaatat taattattta tacaactagt acgagcgcac tatcaacctc    3900
tctaaattcc cttgcccctg tattttcaga tttgtcggac cacggtatat accatc        3956
```

```
<210> SEQ ID NO 2
<211> LENGTH: 2868
<212> TYPE: DNA
<213> ORGANISM: x Triticosecale
<220> FEATURE:
<221> NAME/KEY: CDS
<222> LOCATION: (1)..(2868)

<400> SEQUENCE: 2
```

```
atg gag gcg gct ctg gtg acc gtg gcg acg gga gtc ctc aaa cct gtc        48
Met Glu Ala Ala Leu Val Thr Val Ala Thr Gly Val Leu Lys Pro Val
1               5                   10                  15 ctg ggg aag ctg gcc acc ctg ctc ggc gac gag tac aag cgt ttt aag        96
Leu Gly Lys Leu Ala Thr Leu Leu Gly Asp Glu Tyr Lys Arg Phe Lys
            20                  25                  30 ggt gtg cgc aag gag atc agg tct ctc act cat gaa ctc gcc gcc atg       144
Gly Val Arg Lys Glu Ile Arg Ser Leu Thr His Glu Leu Ala Ala Met
        35                  40                  45 gag gct ttt ctc ctc aag atg tcg gag gag gag gag gat ccc gat gtg       192
Glu Ala Phe Leu Leu Lys Met Ser Glu Glu Glu Glu Asp Pro Asp Val
    50                  55                  60
```

```
cag gat aaa gtc tgg atg aat gag gtg cgg gaa ttg tcc tat gac atg     240
Gln Asp Lys Val Trp Met Asn Glu Val Arg Glu Leu Ser Tyr Asp Met
65              70                  75                  80 gag gac gcc atc gac gac ttc atg caa agc att ggt gac aaa gac gaa     288
Glu Asp Ala Ile Asp Asp Phe Met Gln Ser Ile Gly Asp Lys Asp Glu
                85                  90                  95 aag ccg gat ggc ttc act gag aag atc aag gcc act cta ggc aag ttg     336
Lys Pro Asp Gly Phe Thr Glu Lys Ile Lys Ala Thr Leu Gly Lys Leu
            100                 105                 110 gga aat atg aag gct cgt cat cga att ggc aag gag ata cat gat ctg     384
Gly Asn Met Lys Ala Arg His Arg Ile Gly Lys Glu Ile His Asp Leu
        115                 120                 125 aag aaa cag atc att gag gtg ggc gac agg aat gca agg tac aag gga     432
Lys Lys Gln Ile Ile Glu Val Gly Asp Arg Asn Ala Arg Tyr Lys Gly
    130                 135                 140 cgc gag atc ttc tcc aag gcc gtc aat gcg acc gtt gac cct aga gct     480
Arg Glu Ile Phe Ser Lys Ala Val Asn Ala Thr Val Asp Pro Arg Ala
145                 150                 155                 160 ctt gct atc ttt gag cat gca tca aag ctc gtc gga att gat gaa ccc     528
Leu Ala Ile Phe Glu His Ala Ser Lys Leu Val Gly Ile Asp Glu Pro
                165                 170                 175 aag gct gag ttg atc aag ttg tta act gac gag gat gga gtt gca tca     576
Lys Ala Glu Leu Ile Lys Leu Leu Thr Asp Glu Asp Gly Val Ala Ser
            180                 185                 190 aca caa gaa caa gtg aag atg gtc tgc att gtt gga tcg gga gga atg     624
Thr Gln Glu Gln Val Lys Met Val Cys Ile Val Gly Ser Gly Gly Met
        195                 200                 205 ggc aaa aca act ctt gca aac caa gtg tat caa gag atg aaa gag gaa     672
Gly Lys Thr Thr Leu Ala Asn Gln Val Tyr Gln Glu Met Lys Glu Glu
    210                 215                 220 ttc aag ttt aag gct ttc ata tca gtg tca cga aat cca gat atg atg     720
Phe Lys Phe Lys Ala Phe Ile Ser Val Ser Arg Asn Pro Asp Met Met
225                 230                 235                 240 aat atc ttg aga acc ctc ctc agt gaa att ggg tgt caa gat tat gct     768
Asn Ile Leu Arg Thr Leu Leu Ser Glu Ile Gly Cys Gln Asp Tyr Ala
                245                 250                 255 cac act gaa gca ggg agc ata caa caa cta ata agc aag att acc gat     816
His Thr Glu Ala Gly Ser Ile Gln Gln Leu Ile Ser Lys Ile Thr Asp
            260                 265                 270 tac cta gca gaa aaa agg tat ttt ata gtg att gac gac ata tgg gac     864
Tyr Leu Ala Glu Lys Arg Tyr Phe Ile Val Ile Asp Asp Ile Trp Asp
        275                 280                 285 gtc aaa aca tgg gac gtt att aag tgc gca ttc ccc atg acc aga tgc     912
Val Lys Thr Trp Asp Val Ile Lys Cys Ala Phe Pro Met Thr Arg Cys
    290                 295                 300 ggt ggt gta ata atc acc acc act cgg ctg agt gat gtt gca tgt tcg     960
Gly Gly Val Ile Ile Thr Thr Thr Arg Leu Ser Asp Val Ala Cys Ser
305                 310                 315                 320 tgt cat tca tca atc ggt ggc cat att tat aat ata agg cct ctt aat    1008
Cys His Ser Ser Ile Gly Gly His Ile Tyr Asn Ile Arg Pro Leu Asn
                325                 330                 335 atg gag cac tca aga caa cta ttc tac aga aga tta ttc agc tcc gaa    1056
Met Glu His Ser Arg Gln Leu Phe Tyr Arg Arg Leu Phe Ser Ser Glu
            340                 345                 350 gaa gat tgc cct tca tcg ctc gtg aaa gtt tct tat caa atc ttg gaa    1104
Glu Asp Cys Pro Ser Ser Leu Val Lys Val Ser Tyr Gln Ile Leu Glu
        355                 360                 365 aaa tgt gat ggg ttg cct ttg gca atc att gct ata gct ggt ttg ttg    1152
Lys Cys Asp Gly Leu Pro Leu Ala Ile Ile Ala Ile Ala Gly Leu Leu
    370                 375                 380
```

-continued

```
gct aac aca gga aga tca gag cat caa tgg aac caa gtg aaa gat tca    1200
Ala Asn Thr Gly Arg Ser Glu His Gln Trp Asn Gln Val Lys Asp Ser
385                 390                 395                 400 att ggt cgt gca ctt gaa agg aat cct agt gtc gaa gta atg ata aag    1248
Ile Gly Arg Ala Leu Glu Arg Asn Pro Ser Val Glu Val Met Ile Lys
                405                 410                 415 ata ttg tca ctt agt tac ttt gat ctt cct ccg cat cta aaa aca tgt    1296
Ile Leu Ser Leu Ser Tyr Phe Asp Leu Pro Pro His Leu Lys Thr Cys
            420                 425                 430 ctc ttg tat ctc agt ata ttc ccg gaa gat tct att att gag aag aaa    1344
Leu Leu Tyr Leu Ser Ile Phe Pro Glu Asp Ser Ile Ile Glu Lys Lys
        435                 440                 445 aca cta ata tca aga tgg att gct gaa gga ttc att cga caa gaa ggt    1392
Thr Leu Ile Ser Arg Trp Ile Ala Glu Gly Phe Ile Arg Gln Glu Gly
    450                 455                 460 aga tat act gca tat gag gta gga gtg agg tgt ttt aat gag ctc gtc    1440
Arg Tyr Thr Ala Tyr Glu Val Gly Val Arg Cys Phe Asn Glu Leu Val
465                 470                 475                 480 aac agg agt ttg atc caa cct gtg aag aaa gac gat tat aag ggg aag    1488
Asn Arg Ser Leu Ile Gln Pro Val Lys Lys Asp Asp Tyr Lys Gly Lys
                485                 490                 495 agt tgt cga gtt cac gat ata att ctt gat ttc ata gta tcc aag tcc    1536
Ser Cys Arg Val His Asp Ile Ile Leu Asp Phe Ile Val Ser Lys Ser
            500                 505                 510 att gaa gag aac ttt gtt act ttt gtt ggt gtc ccc agt tta act acc    1584
Ile Glu Glu Asn Phe Val Thr Phe Val Gly Val Pro Ser Leu Thr Thr
        515                 520                 525 gtg aca caa ggc aaa gtc cgc cgt ctc tcc atg caa gtt gaa gag aag    1632
Val Thr Gln Gly Lys Val Arg Arg Leu Ser Met Gln Val Glu Glu Lys
    530                 535                 540 gtg gat tct att ttg cca atg agc ctg ata tta tct cat gtc cga tca    1680
Val Asp Ser Ile Leu Pro Met Ser Leu Ile Leu Ser His Val Arg Ser
545                 550                 555                 560 ctt aac atg ttc ggg aat aca gtg agt att cct tcg atc atg gag ttg    1728
Leu Asn Met Phe Gly Asn Thr Val Ser Ile Pro Ser Ile Met Glu Leu
                565                 570                 575 agg cat ttg cgt gtc ctt gat ttc gga gga aac aga cta ttg gaa aac    1776
Arg His Leu Arg Val Leu Asp Phe Gly Gly Asn Arg Leu Leu Glu Asn
            580                 585                 590 cgt cat ctc gcg tat gta ggg atg ctg ttt cag cta agg tac ctc aac    1824
Arg His Leu Ala Tyr Val Gly Met Leu Phe Gln Leu Arg Tyr Leu Asn
        595                 600                 605 att tac atg aca gca gta agc gag ctc ccg gaa caa atc gga cac tta    1872
Ile Tyr Met Thr Ala Val Ser Glu Leu Pro Glu Gln Ile Gly His Leu
    610                 615                 620 cag tgc tta gag atg ttg gac atc agg cat aca tgg gtg tct gag ctg    1920
Gln Cys Leu Glu Met Leu Asp Ile Arg His Thr Trp Val Ser Glu Leu
625                 630                 635                 640 cca gcc agt att gcc aat ctc ggc aaa ctg gca cac tta ctt ctt agc    1968
Pro Ala Ser Ile Ala Asn Leu Gly Lys Leu Ala His Leu Leu Leu Ser
                645                 650                 655 tca aat act ggc aca aat gtt aag ttt ccc gac gga att gct aag atg    2016
Ser Asn Thr Gly Thr Asn Val Lys Phe Pro Asp Gly Ile Ala Lys Met
            660                 665                 670 caa tca ctg gag gct ttg cat agc gtt aac acc tgc aat cag tca tat    2064
Gln Ser Leu Glu Ala Leu His Ser Val Asn Thr Cys Asn Gln Ser Tyr
        675                 680                 685 aac ttt ctg caa ggg ctt ggt cag cta aag aat ctg agg aag ctg ggc    2112
Asn Phe Leu Gln Gly Leu Gly Gln Leu Lys Asn Leu Arg Lys Leu Gly
```

```
        690              695              700
att aac tat cgg ggt gtt gcc cac gaa gac aag gaa gtt att gct tct    2160
Ile Asn Tyr Arg Gly Val Ala His Glu Asp Lys Glu Val Ile Ala Ser
705              710              715              720 tct ctt ggt aaa cta tgc aca caa aac ctt tgt tct cta act atg tgg    2208
Ser Leu Gly Lys Leu Cys Thr Gln Asn Leu Cys Ser Leu Thr Met Trp
             725              730              735 aat gat gac gac gac ttc ttg cta aat aca tgg tgc act tct ccg ccg    2256
Asn Asp Asp Asp Asp Phe Leu Leu Asn Thr Trp Cys Thr Ser Pro Pro
             740              745              750 ctt aac ctc cga aaa ctt gtc ata tgg ggt tgt ata ttc cca aag gtt    2304
Leu Asn Leu Arg Lys Leu Val Ile Trp Gly Cys Ile Phe Pro Lys Val
         755              760              765 ccg cat tgg gta gga tca ctc gtc aac cta cag aag tta cac ttg gaa    2352
Pro His Trp Val Gly Ser Leu Val Asn Leu Gln Lys Leu His Leu Glu
         770              775              780 gtg ggg aga gga acc cgg cat gaa gat atc tgc atc ctt gga gcc tta    2400
Val Gly Arg Gly Thr Arg His Glu Asp Ile Cys Ile Leu Gly Ala Leu
785              790              795              800 ccc gct ctg ttc act ctg ggt cta cga gga agc gaa aaa cag cct tct    2448
Pro Ala Leu Phe Thr Leu Gly Leu Arg Gly Ser Glu Lys Gln Pro Ser
             805              810              815 tgt gaa aat aga agg ctg gca gtt agt ggt gaa gct ggg ttc cga tgc    2496
Cys Glu Asn Arg Arg Leu Ala Val Ser Gly Glu Ala Gly Phe Arg Cys
             820              825              830 ctg agg aag ttt aaa tac tgg agg tgg ggg gat tgg atg gat ctt atg    2544
Leu Arg Lys Phe Lys Tyr Trp Arg Trp Gly Asp Trp Met Asp Leu Met
             835              840              845 ttt acg gca aaa tgt atg ccc agg cta gaa aaa ctg aag att ata ttt    2592
Phe Thr Ala Lys Cys Met Pro Arg Leu Glu Lys Leu Lys Ile Ile Phe
850              855              860 tac ggc cat gcc gaa gat gag gct ccc atc att cct gct ttc gat ttc    2640
Tyr Gly His Ala Glu Asp Glu Ala Pro Ile Ile Pro Ala Phe Asp Phe
865              870              875              880 ggg atc gaa aac ctg tcc agc ctc act act ttc aaa tgt cac cta ggt    2688
Gly Ile Glu Asn Leu Ser Ser Leu Thr Thr Phe Lys Cys His Leu Gly
             885              890              895 tat ggg cct atg gca acg aaa att gtt gac gct gta aag gct tct ctg    2736
Tyr Gly Pro Met Ala Thr Lys Ile Val Asp Ala Val Lys Ala Ser Leu
             900              905              910 gac aga gta gtt agc gca cat ccc aac cac ctt act cta atc ttc act    2784
Asp Arg Val Val Ser Ala His Pro Asn His Leu Thr Leu Ile Phe Thr
             915              920              925 tat tgt tgt gtg ttt tgt aag agt tat gac tgt ggt ggt cga tgc ctt    2832
Tyr Cys Cys Val Phe Cys Lys Ser Tyr Asp Cys Gly Gly Arg Cys Leu
         930              935              940 ctg tct aga gat ctt cag tca tcc tcc gaa tct act    2868
Leu Ser Arg Asp Leu Gln Ser Ser Ser Glu Ser Thr
945              950              955
```

<210> SEQ ID NO 3
<211> LENGTH: 956
<212> TYPE: PRT
<213> ORGANISM: x Triticosecale

<400> SEQUENCE: 3

```
Met Glu Ala Ala Leu Val Thr Val Ala Thr Gly Val Leu Lys Pro Val
1               5               10              15

Leu Gly Lys Leu Ala Thr Leu Leu Gly Asp Glu Tyr Lys Arg Phe Lys
        20              25              30
```

```
Gly Val Arg Lys Glu Ile Arg Ser Leu Thr His Glu Leu Ala Ala Met
    35                  40                  45

Glu Ala Phe Leu Leu Lys Met Ser Glu Glu Glu Asp Pro Asp Val
    50                  55                  60

Gln Asp Lys Val Trp Met Asn Glu Val Arg Glu Leu Ser Tyr Asp Met
65                  70                  75                  80

Glu Asp Ala Ile Asp Asp Phe Met Gln Ser Ile Gly Asp Lys Asp Glu
                85                  90                  95

Lys Pro Asp Gly Phe Thr Glu Lys Ile Lys Ala Thr Leu Gly Lys Leu
                100                 105                 110

Gly Asn Met Lys Ala Arg His Arg Ile Gly Lys Glu Ile His Asp Leu
                115                 120                 125

Lys Lys Gln Ile Ile Glu Val Gly Asp Arg Asn Ala Arg Tyr Lys Gly
    130                 135                 140

Arg Glu Ile Phe Ser Lys Ala Val Asn Ala Thr Val Asp Pro Arg Ala
145                 150                 155                 160

Leu Ala Ile Phe Glu His Ala Ser Lys Leu Val Gly Ile Asp Glu Pro
                165                 170                 175

Lys Ala Glu Leu Ile Lys Leu Leu Thr Asp Glu Asp Gly Val Ala Ser
                180                 185                 190

Thr Gln Glu Gln Val Lys Met Val Cys Ile Val Gly Ser Gly Gly Met
                195                 200                 205

Gly Lys Thr Thr Leu Ala Asn Gln Val Tyr Gln Glu Met Lys Glu Glu
    210                 215                 220

Phe Lys Phe Lys Ala Phe Ile Ser Val Ser Arg Asn Pro Asp Met Met
225                 230                 235                 240

Asn Ile Leu Arg Thr Leu Leu Ser Glu Ile Gly Cys Gln Asp Tyr Ala
                245                 250                 255

His Thr Glu Ala Gly Ser Ile Gln Gln Leu Ile Ser Lys Ile Thr Asp
                260                 265                 270

Tyr Leu Ala Glu Lys Arg Tyr Phe Ile Val Ile Asp Asp Ile Trp Asp
                275                 280                 285

Val Lys Thr Trp Asp Val Ile Lys Cys Ala Phe Pro Met Thr Arg Cys
    290                 295                 300

Gly Gly Val Ile Ile Thr Thr Thr Arg Leu Ser Asp Val Ala Cys Ser
305                 310                 315                 320

Cys His Ser Ser Ile Gly Gly His Ile Tyr Asn Ile Arg Pro Leu Asn
                325                 330                 335

Met Glu His Ser Arg Gln Leu Phe Tyr Arg Arg Leu Phe Ser Ser Glu
                340                 345                 350

Glu Asp Cys Pro Ser Ser Leu Val Lys Val Ser Tyr Gln Ile Leu Glu
                355                 360                 365

Lys Cys Asp Gly Leu Pro Leu Ala Ile Ile Ala Ile Ala Gly Leu Leu
    370                 375                 380

Ala Asn Thr Gly Arg Ser Glu His Gln Trp Asn Gln Val Lys Asp Ser
385                 390                 395                 400

Ile Gly Arg Ala Leu Glu Arg Asn Pro Ser Val Glu Val Met Ile Lys
                405                 410                 415

Ile Leu Ser Leu Ser Tyr Phe Asp Leu Pro Pro His Leu Lys Thr Cys
                420                 425                 430

Leu Leu Tyr Leu Ser Ile Phe Pro Glu Asp Ser Ile Ile Glu Lys Lys
    435                 440                 445
```

-continued

```
Thr Leu Ile Ser Arg Trp Ile Ala Glu Gly Phe Ile Arg Gln Glu Gly
    450                 455                 460

Arg Tyr Thr Ala Tyr Glu Val Gly Val Arg Cys Phe Asn Glu Leu Val
465                 470                 475                 480

Asn Arg Ser Leu Ile Gln Pro Val Lys Lys Asp Asp Tyr Lys Gly Lys
                485                 490                 495

Ser Cys Arg Val His Asp Ile Ile Leu Asp Phe Ile Val Ser Lys Ser
            500                 505                 510

Ile Glu Glu Asn Phe Val Thr Phe Val Gly Val Pro Ser Leu Thr Thr
        515                 520                 525

Val Thr Gln Gly Lys Val Arg Arg Leu Ser Met Gln Val Glu Glu Lys
    530                 535                 540

Val Asp Ser Ile Leu Pro Met Ser Leu Ile Leu Ser His Val Arg Ser
545                 550                 555                 560

Leu Asn Met Phe Gly Asn Thr Val Ser Ile Pro Ser Ile Met Glu Leu
                565                 570                 575

Arg His Leu Arg Val Leu Asp Phe Gly Gly Asn Arg Leu Leu Glu Asn
            580                 585                 590

Arg His Leu Ala Tyr Val Gly Met Leu Phe Gln Leu Arg Tyr Leu Asn
        595                 600                 605

Ile Tyr Met Thr Ala Val Ser Glu Leu Pro Glu Gln Ile Gly His Leu
    610                 615                 620

Gln Cys Leu Glu Met Leu Asp Ile Arg His Thr Trp Val Ser Glu Leu
625                 630                 635                 640

Pro Ala Ser Ile Ala Asn Leu Gly Lys Leu Ala His Leu Leu Leu Ser
                645                 650                 655

Ser Asn Thr Gly Thr Asn Val Lys Phe Pro Asp Gly Ile Ala Lys Met
            660                 665                 670

Gln Ser Leu Glu Ala Leu His Ser Val Asn Thr Cys Asn Gln Ser Tyr
        675                 680                 685

Asn Phe Leu Gln Gly Leu Gly Gln Leu Lys Asn Leu Arg Lys Leu Gly
    690                 695                 700

Ile Asn Tyr Arg Gly Val Ala His Glu Asp Lys Glu Val Ile Ala Ser
705                 710                 715                 720

Ser Leu Gly Lys Leu Cys Thr Gln Asn Leu Cys Ser Leu Thr Met Trp
                725                 730                 735

Asn Asp Asp Asp Asp Phe Leu Leu Asn Thr Trp Cys Thr Ser Pro Pro
            740                 745                 750

Leu Asn Leu Arg Lys Leu Val Ile Trp Gly Cys Ile Phe Pro Lys Val
            755                 760                 765

Pro His Trp Val Gly Ser Leu Val Asn Leu Gln Lys Leu His Leu Glu
    770                 775                 780

Val Gly Arg Gly Thr Arg His Glu Asp Ile Cys Ile Leu Gly Ala Leu
785                 790                 795                 800

Pro Ala Leu Phe Thr Leu Gly Leu Arg Gly Ser Glu Lys Gln Pro Ser
                805                 810                 815

Cys Glu Asn Arg Arg Leu Ala Val Ser Gly Glu Ala Gly Phe Arg Cys
            820                 825                 830

Leu Arg Lys Phe Lys Tyr Trp Arg Trp Gly Asp Trp Met Asp Leu Met
        835                 840                 845

Phe Thr Ala Lys Cys Met Pro Arg Leu Glu Lys Leu Lys Ile Ile Phe
    850                 855                 860

Tyr Gly His Ala Glu Asp Glu Ala Pro Ile Ile Pro Ala Phe Asp Phe
```

```
865              870              875              880

Gly Ile Glu Asn Leu Ser Ser Leu Thr Thr Phe Lys Cys His Leu Gly
            885              890              895

Tyr Gly Pro Met Ala Thr Lys Ile Val Asp Ala Val Lys Ala Ser Leu
            900              905              910

Asp Arg Val Val Ser Ala His Pro Asn His Leu Thr Leu Ile Phe Thr
            915              920              925

Tyr Cys Cys Val Phe Cys Lys Ser Tyr Asp Cys Gly Gly Arg Cys Leu
        930              935              940

Leu Ser Arg Asp Leu Gln Ser Ser Ser Glu Ser Thr
945              950              955
```

```
<210> SEQ ID NO 4
<211> LENGTH: 3778
<212> TYPE: DNA
<213> ORGANISM: x Triticosecale

<400> SEQUENCE: 4
atggaggcgg ctctggtgac cgtggcgacg ggagtcctca aacctgtcct ggggaagctg     60
gccaccctgc tcggcgacga gtacaagcgt tttaagggtg tgcgcaagga gatcaggtct    120
ctcactcatg aactcgccgc catggaggct tttctcctca agatgtcgga ggaggaggag    180
gatcccgatg tgcaggataa agtctggatg aatgaggtgc gggaattgtc ctatgacatg    240
gaggacgcca tcgacgactt catgcaaagc attggtgaca agacgaaaa gccggatggc    300 ttcactgaga agatcaaggc cactctaggc aagttgggaa atatgaaggc tcgtcatcga    360
attggcaagg agatacatga tctgaagaaa cagatcattg aggtgggcga caggaatgca    420
aggtacaagg gacgcgagat cttctccaag gccgtcaatg cgaccgttga ccctagagct    480
cttgctatct ttgagcatgc atcaaagctc gtcggaattg atgaacccaa ggctgagttg    540
atcaagttgt taactgacga ggatggagtt gcatcaacac aagaacaagt gaagatggtc    600
tgcattgttg atcgggagg aatgggcaaa acaactcttg caaaccaagt gtatcaagag    660
atgaaagagg aattcaagtt taaggctttc tatcagtgt cacgaaatcc agatatgatg    720
aatatcttga aaccctcct cagtgaaatt gggtgtcaag attatgctca cactgaagca    780
gggagcatac aacaactaat aagcaagatt accgattacc tagcagaaaa aaggtactat    840
tatatttctt taaactcact tctcgcccat agaaagttaa attaagaatt ctcacataga    900
aaaaacactc ctaataaaga atcaaaataa ttatataatt aaattatata ctttttgggt    960
gaaaattaat tgccaaatgt atggaagccc ttatttgcat gtactttact acttcctccg   1020
ttcctaaata taagtctttg gagagatttc actatggacc acatacgaag caaaatgagt   1080
gaatctacac tctaaaatgc atctatatac atccgtatgt ggttcatggt gaaatctcta   1140
gaaagactta tatttaggaa cggagggagt agttaactag gttgttgtat ttggagggaa   1200
aataagtctt atataggtag gaacatttga ttagtaggta ttcggcatgt atgtgcatct   1260
cagaatgcat atagactaaa agacaatctt ttccgcaata aagaaatatc atcaatcttc   1320
aatcaagcaa gtatgctact ccctccgtcc caaaattctt gtcttagatt tgtctaaata   1380
cagatgtatc aagtcacatt ttagtattag aaacatccgt atctgggcaa atctaagaca   1440
agaattttgg gacggaggga gtacatgata tgtaccactc taagtgctta gagctctttt   1500
gctcttatat ggcctatcta ggaaaacata ttttgtttag taagtgctta gagtagaaac   1560
actatatagg tattttctag ccatgtggcc ctgtttaagt tgcatagtac cctagagccg   1620
```

-continued

```
atccattatc ttttgcatgt tgccaatgag aacatggaaa tttctctttc ttcttatttt      1680
gcttgtacgc ttcgttttaa cacatcatac taactattac tactaaaaaa tcatgtgcag      1740
gtattttata gtgattgacg acatatggga cgtcaaaaca tgggacgtta ttaagtgcgc      1800
attccccatg accagatgcg gtggtgtaat aatcaccacc actcggctga gtgatgttgc      1860
atgttcgtgt cattcatcaa tcggtggcca tatttataat ataaggcctc ttaatatgga      1920
gcactcaaga caactattct acagaagatt attcagctcc gaagaagatt gcccttcatc      1980
gctcgtgaaa gtttcttatc aaatcttgga aaaatgtgat gggttgcctt tggcaatcat      2040
tgctatagct ggtttgttgg ctaacacagg aagatcagag catcaatgga accaagtgaa      2100
agattcaatt ggtcgtgcac ttgaaaggaa tcctagtgtc gaagtaatga taaagatatt      2160
gtcacttagt tactttgatc ttcctccgca tctaaaaaca tgtctcttgt atctcagtat      2220
attcccggaa gattctatta ttgagaagaa aacactaata tcaagatgga ttgctgaagg      2280
attcattcga caagaaggta gatatactgc atatgaggta ggagtgaggt gttttaatga      2340
gctcgtcaac aggagtttga tccaacctgt gaagaaagac gattataagg ggaagagttg      2400
tcgagttcac gatataattc ttgatttcat agtatccaag tccattgaag agaactttgt      2460
tacttttgtt ggtgtcccca gtttaactac cgtgacacaa ggcaaagtcc gccgtctctc      2520
catgcaagtt gaagagaagg tggattctat tttgccaatg agcctgatat tatctcatgt      2580
ccgatcactt aacatgttcg ggaatacagt gagtattcct tcgatcatgg agttgaggca      2640
tttgcgtgtc cttgatttcg gaggaaacag actattggaa aaccgtcatc tcgcgtatgt      2700
agggatgctg tttcagctaa ggtacctcaa catttacatg acagcagtaa gcgagctccc      2760
ggaacaaatc ggacacttac agtgcttaga gatgttggac atcaggcata catgggtgtc      2820
tgagctgcca gccagtattg ccaatctcgg caaactggca cacttacttc ttagctcaaa      2880
tactggcaca aatgttaagt ttcccgacgg aattgctaag atgcaatcac tggaggcttt      2940
gcatagcgtt aacacctgca atcagtcata taactttctg caagggcttg gtcagctaaa      3000
gaatctgagg aagctgggca ttaactatcg gggtgttgcc cacgaagaca aggaagttat      3060
tgcttcttct cttggtaaac tatgcacaca aaacctttgt tctctaacta tgtggaatga      3120
tgacgacgac ttcttgctaa atacatggtg cacttctccg ccgcttaacc tccgaaaact      3180
tgtcatatgg ggttgtatat tcccaaaggt tccgcattgg gtaggatcac tcgtcaacct      3240
acagaagtta cacttggaag tggggagagg aacccggcat gaagatatct gcatccttgg      3300
agccttaccc gctctgttca ctctgggtct acgaggaagc gaaaaacagc cttcttgtga      3360
aaatagaagg ctggcagtta gtggtgaagc tgggttccga tgcctgagga agtttaaata      3420
ctggaggtgg ggggattgga tggatcttat gtttacggca aaatgtatgc ccaggctaga      3480
aaaactgaag attatatttt acggccatgc cgaagatgag gctcccatca ttcctgcttt      3540
cgatttcggg atcgaaaacc tgtccagcct cactactttc aaatgtcacc taggttatgg      3600
gcctatggca acgaaaattg ttgacgctgt aaaggcttct ctggacagag tagttagcgc      3660
acatcccaac caccttactc taatcttcac ttattgttgt gtgtttttgta agagttatga      3720 ctgtggtggt cgatgccttc tgtctagaga tcttcagtca tcctccgaat ctacttga      3778
```

<210> SEQ ID NO 5
<211> LENGTH: 435
<212> TYPE: DNA
<213> ORGANISM: Puccinia graminis fsp. tritici
<220> FEATURE:
<221> NAME/KEY: CDS

```
<222> LOCATION: (1)..(435)

<400> SEQUENCE: 5 atg cat tac atc acc ccc ata atc ctt atg tca att gga caa ttt ctt          48
Met His Tyr Ile Thr Pro Ile Ile Leu Met Ser Ile Gly Gln Phe Leu
1               5                   10                  15 ggc ata tta ttg gga gca gga ggt ctt gtg ggt gca atg aca cca cat          96
Gly Ile Leu Leu Gly Ala Gly Gly Leu Val Gly Ala Met Thr Pro His
                20                  25                  30 cac caa agc aat tgc aac tcc cca tct ttg aca ttt ccc agg ttc att         144
His Gln Ser Asn Cys Asn Ser Pro Ser Leu Thr Phe Pro Arg Phe Ile
            35                  40                  45 gga aaa tgt gac tcc tgc cag ctc cat acc aaa gct acc aac ctg gtg         192
Gly Lys Cys Asp Ser Cys Gln Leu His Thr Lys Ala Thr Asn Leu Val
        50                  55                  60 agc tgc acc tct tgt agg aaa tcc tca ttg gta tat gaa gaa tgt tcc         240
Ser Cys Thr Ser Cys Arg Lys Ser Ser Leu Val Tyr Glu Glu Cys Ser
65                  70                  75                  80 acc aaa ggc tgt cct gct aat tgg cac aaa agc acc tgt caa gaa ccc         288
Thr Lys Gly Cys Pro Ala Asn Trp His Lys Ser Thr Cys Gln Glu Pro
                85                  90                  95 aag ttc aat aga ggt att ctg tcc tgt tac tgt gag aac tgc cag cag         336
Lys Phe Asn Arg Gly Ile Leu Ser Cys Tyr Cys Glu Asn Cys Gln Gln
                100                 105                 110 cac acc aag gaa aaa cag aca att tcc tgc aaa aat tgt aag aat tca         384
His Thr Lys Glu Lys Gln Thr Ile Ser Cys Lys Asn Cys Lys Asn Ser
            115                 120                 125 gcc acc acc ttc tca cat tgt tca agc cca gag tgt cac agc aga tgg         432
Ala Thr Thr Phe Ser His Cys Ser Ser Pro Glu Cys His Ser Arg Trp
        130                 135                 140 taa                                                                     435

<210> SEQ ID NO 6
<211> LENGTH: 144
<212> TYPE: PRT
<213> ORGANISM: Puccinia graminis fsp. tritici

<400> SEQUENCE: 6

Met His Tyr Ile Thr Pro Ile Ile Leu Met Ser Ile Gly Gln Phe Leu
1               5                   10                  15

Gly Ile Leu Leu Gly Ala Gly Gly Leu Val Gly Ala Met Thr Pro His
                20                  25                  30

His Gln Ser Asn Cys Asn Ser Pro Ser Leu Thr Phe Pro Arg Phe Ile
            35                  40                  45

Gly Lys Cys Asp Ser Cys Gln Leu His Thr Lys Ala Thr Asn Leu Val
        50                  55                  60

Ser Cys Thr Ser Cys Arg Lys Ser Ser Leu Val Tyr Glu Glu Cys Ser
65                  70                  75                  80

Thr Lys Gly Cys Pro Ala Asn Trp His Lys Ser Thr Cys Gln Glu Pro
                85                  90                  95

Lys Phe Asn Arg Gly Ile Leu Ser Cys Tyr Cys Glu Asn Cys Gln Gln
                100                 105                 110

His Thr Lys Glu Lys Gln Thr Ile Ser Cys Lys Asn Cys Lys Asn Ser
            115                 120                 125

Ala Thr Thr Phe Ser His Cys Ser Ser Pro Glu Cys His Ser Arg Trp
        130                 135                 140

<210> SEQ ID NO 7
```

```
<211> LENGTH: 435
<212> TYPE: DNA
<213> ORGANISM: Puccinia graminis fsp. tritici
<220> FEATURE:
<221> NAME/KEY: CDS
<222> LOCATION: (1)..(435)

<400> SEQUENCE: 7 atg cat tac atc acc ccc ata atc ctt atg tca att gga aaa ttt ctt      48
Met His Tyr Ile Thr Pro Ile Ile Leu Met Ser Ile Gly Lys Phe Leu
1               5                   10                  15 gga atg ata ttg gga gca gga agt ctt gtg ggt gca atg aca cca cat      96
Gly Met Ile Leu Gly Ala Gly Ser Leu Val Gly Ala Met Thr Pro His
                20                  25                  30 cac caa agc aat tgc aac tcc cca tgt ttg gta ttt gtc aca ttc acc     144
His Gln Ser Asn Cys Asn Ser Pro Cys Leu Val Phe Val Thr Phe Thr
            35                  40                  45 aaa aaa tgt gac tcc tgc cag ttc aat aca aaa ttc act aac ctg atg     192
Lys Lys Cys Asp Ser Cys Gln Phe Asn Thr Lys Phe Thr Asn Leu Met
        50                  55                  60 agc tgc acc tct tgt agg aaa tcc tca gtg gta tat gaa gaa tgt tcc     240
Ser Cys Thr Ser Cys Arg Lys Ser Ser Val Val Tyr Glu Glu Cys Ser
65                  70                  75                  80 acc aaa ggc tgt cct gct aat tgg cac aaa agt acc tgt caa gaa ccc     288
Thr Lys Gly Cys Pro Ala Asn Trp His Lys Ser Thr Cys Gln Glu Pro
                85                  90                  95 aag ttt gag aga ggt gtt cta cac agc ctc tgt gca aac tgc cag aag     336
Lys Phe Glu Arg Gly Val Leu His Ser Leu Cys Ala Asn Cys Gln Lys
                100                 105                 110 cac aca aag gca aca ccg aca att tcc tgc aaa aat tgt aag aat tca     384
His Thr Lys Ala Thr Pro Thr Ile Ser Cys Lys Asn Cys Lys Asn Ser
            115                 120                 125 gcc agc acc tac cca tat tgt tca agc cca gag tgt cac aga aga tgg     432
Ala Ser Thr Tyr Pro Tyr Cys Ser Ser Pro Glu Cys His Arg Arg Trp
        130                 135                 140 taa                                                                 435

<210> SEQ ID NO 8
<211> LENGTH: 144
<212> TYPE: PRT
<213> ORGANISM: Puccinia graminis fsp. tritici

<400> SEQUENCE: 8

Met His Tyr Ile Thr Pro Ile Ile Leu Met Ser Ile Gly Lys Phe Leu
1               5                   10                  15

Gly Met Ile Leu Gly Ala Gly Ser Leu Val Gly Ala Met Thr Pro His
                20                  25                  30

His Gln Ser Asn Cys Asn Ser Pro Cys Leu Val Phe Val Thr Phe Thr
            35                  40                  45

Lys Lys Cys Asp Ser Cys Gln Phe Asn Thr Lys Phe Thr Asn Leu Met
        50                  55                  60

Ser Cys Thr Ser Cys Arg Lys Ser Ser Val Val Tyr Glu Glu Cys Ser
65                  70                  75                  80

Thr Lys Gly Cys Pro Ala Asn Trp His Lys Ser Thr Cys Gln Glu Pro
                85                  90                  95

Lys Phe Glu Arg Gly Val Leu His Ser Leu Cys Ala Asn Cys Gln Lys
                100                 105                 110

His Thr Lys Ala Thr Pro Thr Ile Ser Cys Lys Asn Cys Lys Asn Ser
            115                 120                 125
```

-continued

```
Ala Ser Thr Tyr Pro Tyr Cys Ser Ser Pro Glu Cys His Arg Arg Trp
   130                 135                 140
```

```
<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
cctgttcgat cactggtcg                                                19
```

```
<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gtgaagatgg tctgcattgt tggatcg                                       27
```

```
<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
gatggtatat accgtggtcc gacaaat                                       27
```

```
<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cggaggttaa gcggcggaga                                               20
```

```
<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
ggttttgtgt gcatagttta ccaagag                                       27
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
atgaacccaa ggctgagttg                                               20
```

```
<210> SEQ ID NO 15
<211> LENGTH: 20
<212> TYPE: DNA
```

-continued

```
<213> ORGANISM: Artificial Sequence
<220> FEATURE:
<223> OTHER INFORMATION: Primer

<400> SEQUENCE: 15
acatgcaaat aagggcttcc                                          20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gtaaggctcc aaggatgcag                                          20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
taagtttccc gacggaattg                                          20

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
aagaacaagt gaagatggtc tgc                                      23

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
ttctgtagaa tagttgtctt gagtgctc                                 28

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tacgaggaag cgaaaaacag c                                        21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
atcttctcag tgaagccatc                                          20
```

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
aaatgtgact tgatacatct g                                              21

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
atagtgattg acgacatatg g                                              21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gattcattcg acaagaaggt                                                20

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
attcagattt aagagtcttg attgagtccc catg                                34

<210> SEQ ID NO 26
<211> LENGTH: 29
<212> TYPE: DNA
<213> ORGANISM: Artificial Sequence
<220> FEATURE:
<223> OTHER INFORMATION: Primer

<400> SEQUENCE: 26
caccatgcaa ttagccagtg tcttatgtg                                      29

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
gtcttcctac ctgtgttggc gccttgcaaa atg                                 33

<210> SEQ ID NO 28
<211> LENGTH: 35
<212> TYPE: DNA
<213> ORGANISM: Artificial Sequence
<220> FEATURE:

-continued

<223> OTHER INFORMATION: Primer

<400> SEQUENCE: 28
caccatgatg cattcaatta tctttcaaac actcc                          35

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
ttaccatctt ctgtgacact ctggg                                    25

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
ttaccatctg ctgtgacact ctgg                                     24

<210> SEQ ID NO 31
<211> LENGTH: 34
<212> TYPE: DNA
<213> ORGANISM: Artificial Sequence
<220> FEATURE:
<223> OTHER INFORMATION: Primer

<400> SEQUENCE: 31
caccatggca atgacaccac atcaccaaag caat                          34

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
ccatcttctg tgacactctg ggcttg                                   26

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33
ccatctgctg tgacactctg ggcttg                                   26

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
caccatgcat tacatcaccc ccataatcct t                             31

-continued

```
<210> SEQ ID NO 35
<211> LENGTH: 33
<212> TYPE: DNA
<213> ORGANISM: Artificial Sequence
<220> FEATURE:
<223> OTHER INFORMATION: Primer

<400> SEQUENCE: 35
caccatggca ggaagtcttg tgggtgcaat gac                                   33

<210> SEQ ID NO 36
<211> LENGTH: 33
<212> TYPE: DNA
<213> ORGANISM: Artificial Sequence
<220> FEATURE:
<223> OTHER INFORMATION: Primer

<400> SEQUENCE: 36
caccatggca ggaggtcttg tgggtgcaat gac                                   33

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
aagtggataa cgtactctgc acaac                                           25

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
agtgactgca attcaccaat atttcg                                          26

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
aacattcagt gcgaggaatg gggag                                           25
```